US010261072B2

(12) United States Patent
Tateyama et al.

(10) Patent No.: US 10,261,072 B2
(45) Date of Patent: Apr. 16, 2019

(54) SAMPLE ANALYZER AND SAMPLE ANALYZING METHOD

(71) Applicant: Sysmex Corporation, Kobe-shi, Hyogo (JP)

(72) Inventors: Shota Tateyama, Kobe (JP); Tetsuya Kaneko, Kobe (JP)

(73) Assignee: SYSMEX CORPORATION, Kobe-Shi, Hyogo (JP)

( * ) Notice: Subject to any disclaimer, the term of this patent is extended or adjusted under 35 U.S.C. 154(b) by 424 days.

(21) Appl. No.: 14/835,002

(22) Filed: Aug. 25, 2015

(65) Prior Publication Data

US 2016/0061821 A1 Mar. 3, 2016

(30) Foreign Application Priority Data

Aug. 27, 2014 (JP) ................. 2014-173341

(51) Int. Cl.
*G01N 33/50* (2006.01)
*G01N 21/49* (2006.01)
*G01N 21/64* (2006.01)
*G01N 15/14* (2006.01)
G01N 15/00 (2006.01)

(52) U.S. Cl.
CPC ..... *G01N 33/5094* (2013.01); *G01N 15/1429* (2013.01); *G01N 15/1459* (2013.01); *G01N 21/49* (2013.01); *G01N 21/6428* (2013.01); G01N 2015/0069 (2013.01); G01N 2015/0073 (2013.01); G01N 2021/6439 (2013.01); G01N 2201/061 (2013.01)

(58) Field of Classification Search
None
See application file for complete search history.

(56) References Cited

U.S. PATENT DOCUMENTS

| 5,516,695 | A | | 5/1996 | Kim et al. | |
|---|---|---|---|---|---|
| 5,559,037 | A | | 9/1996 | Kim et al. | |
| 5,693,484 | A | * | 12/1997 | Nakamoto | ............... C12Q 1/68 209/581 |
| 5,888,823 | A | * | 3/1999 | Matsumoto | ........ G01N 15/1012 436/10 |
| 5,891,733 | A | | 4/1999 | Inoue | |
| 6,165,740 | A | * | 12/2000 | Fukuda | ..................... C12Q 1/04 435/283.1 |

(Continued)

FOREIGN PATENT DOCUMENTS

| CN | 101173888 A | 5/2008 |
|---|---|---|
| CN | 101236194 A | 8/2008 |

(Continued)

*Primary Examiner* — Jill A Warden
*Assistant Examiner* — Brittany I Fisher
(74) *Attorney, Agent, or Firm* — Brinks Gilson & Lione

(57) ABSTRACT

Disclosed is a sample analyzer for analyzing a sample, including: a preparing unit that mixes a sample, a surfactant-containing diluent, and a nucleic acid staining reagent to prepare a measurement specimen in which nucleic acids of nucleated cells are stained and red blood cells are hemolyzed; a detecting unit that irradiates particles included in the measurement specimen with light to receive scattered light and fluorescence light emitted from the particles and output a detection signal; and a processing unit that counts white blood cells and fungi in the sample based on the detection signal.

16 Claims, 19 Drawing Sheets

(56) References Cited

U.S. PATENT DOCUMENTS

| | | | |
|---|---|---|---|
| 8,501,482 B2* | 8/2013 | Tanaka | G01N 15/1459 436/166 |
| 2006/0073601 A1 | 4/2006 | Kawashima et al. | |
| 2007/0013906 A1* | 1/2007 | Kawate | G01N 15/1012 356/243.2 |
| 2009/0323062 A1* | 12/2009 | Ariyoshi | G01N 15/1459 356/337 |
| 2010/0021878 A1 | 1/2010 | Kim et al. | |
| 2010/0047856 A1* | 2/2010 | Takata | C12Q 1/04 435/39 |
| 2010/0247383 A1* | 9/2010 | Okubo | G01N 27/06 422/82.02 |
| 2012/0225475 A1* | 9/2012 | Wagner | G01N 15/14 435/288.7 |
| 2013/0177950 A1* | 7/2013 | Osada | C07D 493/10 435/118 |
| 2014/0154677 A1 | 6/2014 | Ishisaka et al. | |

FOREIGN PATENT DOCUMENTS

| | | | | |
|---|---|---|---|---|
| CN | 101620223 A | 1/2010 | | |
| EP | 0585754 A1 | 3/1994 | | |
| EP | 2703813 B1 * | 5/2014 | | G01N 33/49 |
| JP | 09-329596 A | 12/1997 | | |
| JP | H09329596 | 12/1997 | | |
| JP | 11-23446 A | 1/1999 | | |
| JP | H11023446 | 1/1999 | | |
| JP | 2007-309728 A | 11/2007 | | |
| JP | 2013-92433 A | 5/2013 | | |

* cited by examiner

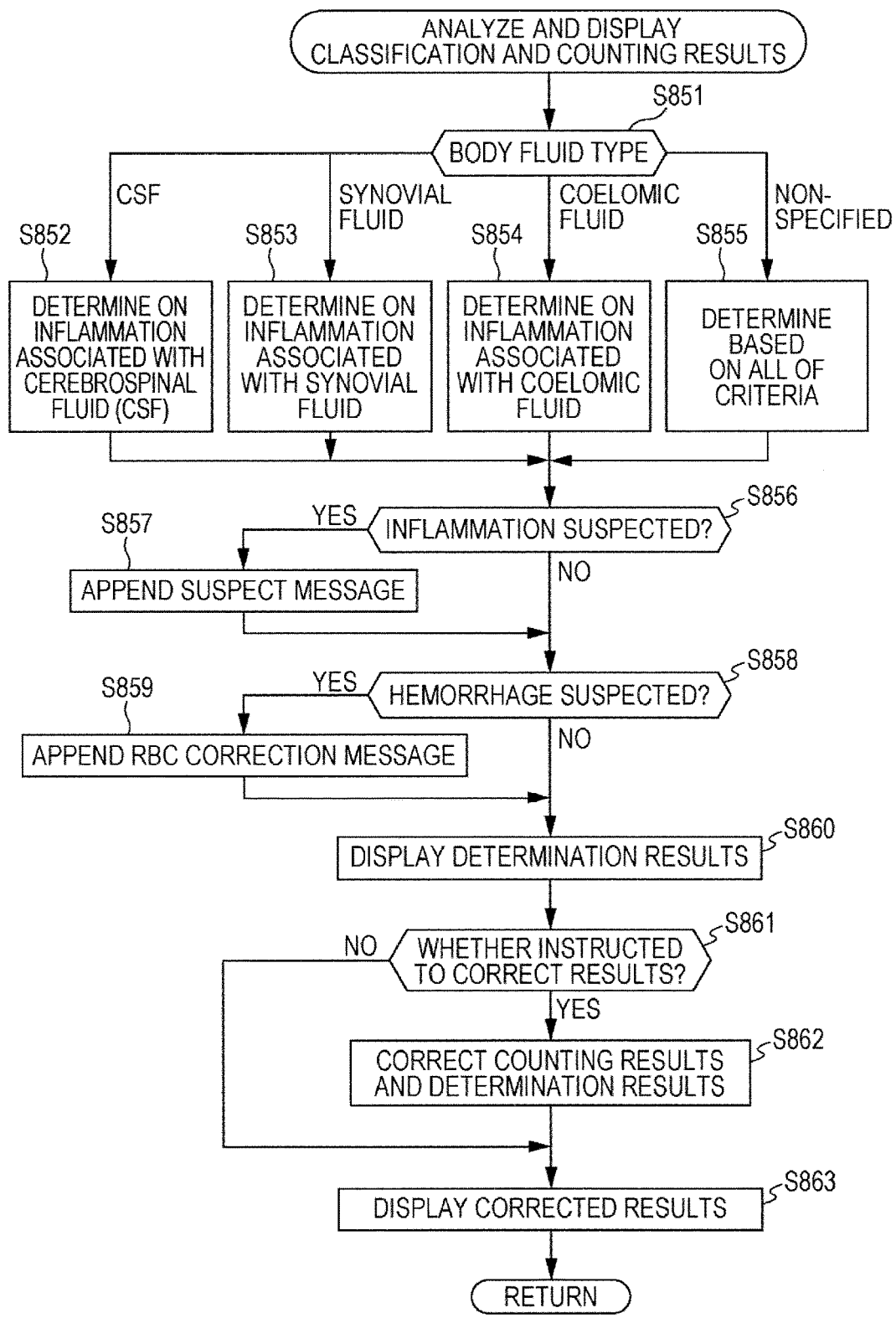

SAMPLE ANALYZER AND SAMPLE ANALYZING METHOD

CROSS REFERENCE TO RELATED APPLICATIONS

This application claims priority from prior Japanese Patent Application No. 2014-173341, filed on Aug. 27, 2014, entitled "SAMPLE ANALYZER AND SAMPLE ANALYZING METHOD", the entire contents of which are incorporated herein by reference.

TECHNICAL FIELD

The present invention relates to a sample analyzer and a sample analyzing method.

BACKGROUND

US2010/0021878A1 discloses a method for counting white blood cells, erythroblasts, and bacteria in a body fluid using an automatic blood analyzer.

The technique described in US2010/0021878A1 is only directed at counting white blood cells, erythroblasts, and bacteria in a body fluid. For appropriate diagnosis and treatment, it is desirable to obtain more useful information through body fluid analysis.

SUMMARY OF THE INVENTION

The scope of the present invention is defined solely by the appended claims, and is not affected to any degree by the statements within this summary.

A first aspect of the invention provides a sample analyzer for analyzing a sample, comprising: a preparing unit that mixes a sample, a surfactant-containing diluent, and a nucleic acid staining reagent to prepare a measurement specimen in which nucleic acids of nucleated cells are stained and red blood cells are hemolyzed; a detecting unit that irradiates particles included in the measurement specimen with light to receive scattered light and fluorescence light emitted from the particles and output a detection signal; and a processing unit that counts white blood cells and fungi in the sample based on the detection signal.

A second aspect of the invention provides a sample analyzing method, comprising: mixing a sample, a surfactant-containing diluent, and a nucleic acid staining reagent to prepare a measurement specimen in which nucleic acids of nucleic cells are stained and red blood cells are hemolyzed; irradiating particles included in the measurement specimen to receive scattered light and fluorescence light emitted from the particles and output a detection signal; and counting white blood cells and fungi in the sample based on the detection signal.

A third another aspect of the invention provides a sample analyzer, comprising: a setting section that receives one of a urine analysis mode for analyzing a urine sample and a body fluid analysis mode for analyzing a body fluid sample other than blood and urine; a preparing unit that mixes the urine sample and a reagent to prepare a first measurement specimen in the urine analysis mode and mixes the body fluid sample and a reagent to prepare a second measurement specimen in the body fluid analysis mode; a detecting unit that irradiates particles included in each of the first and second measurement specimens to receive light emitted from the particles and output a detection signal; and a processing unit that classifies white blood cells in the body fluid sample into mononuclear leukocytes and polymorphonuclear leukocytes and counts at least one of bacteria and fungi in the body fluid sample based on the detection signal outputted from the detecting unit in the body fluid analysis mode.

A fourth aspect of the invention provides a sample analyzer for analyzing a body fluid sample other than blood and urine, the analyzer comprising: a preparing unit that mixes a body fluid sample and a reagent to prepare a measurement specimen; a detecting unit that detects particles included in the measurement specimen and outputs a signal; and a processing unit that analyzes plural types of particles included in the body fluid sample based on the signal outputted from the detecting unit, and determines an inflammation suspected based on a combination of types of particles exhibiting abnormal values.

A fifth aspect of the invention provides a sample analyzer for analyzing a body fluid sample other than blood and urine, the analyzer comprising: a preparing unit that mixes a body fluid sample and a reagent to prepare a measurement specimen; a detecting unit that detects particles included in the measurement specimen and outputs a signal; and a processing unit that analyzes particles included in the body fluid sample based on the signal outputted from the detecting unit, and receives a designation of a type of the body fluid sample to determine an inflammation suspected from an obtained analysis result based on a criterion according to the designated type of the body fluid sample.

A sixth aspect of the invention provides a sample analyzer for analyzing a body fluid sample other than blood and urine, the analyzer comprising: a preparing unit that prepares, from a body fluid sample, a first measurement specimen in which red blood cells are not hemolyzed and a second measurement specimen in which red blood cells are hemolyzed and nucleic acids of nucleic cells are stained; a detecting unit that detects particles included in each of the first and second measurement specimens and outputs a signal; and a processing unit that counts red blood cells included in the first measurement specimen and white blood cells included in the second measurement specimen based on the signal outputted from the detecting unit, and corrects the count of white blood cells based on the count of red blood cells when the count of red blood cells is equal to or greater than a predetermined value.

A seventh aspect of the invention provides a sample analyzer for analyzing a sample, the analyzer comprising: a preparing unit that mixes a sample and a nucleic acid staining reagent to prepare a measurement specimen; a detecting unit that irradiates particles included in the measurement specimen with light to receive light emitted from the particles and output a detection signal; and a processing unit that obtains plural characteristic parameters from the detection signal outputted from the detecting unit, distinguishes white blood cells in the sample at least from large nucleated cells and fungi based on a first combination of plural characteristic parameters reflecting particle sizes and nucleic acid amounts, and classifies the white blood cells in the sample at least into mononuclear leukocytes and polymorphonuclear leukocytes based on a second combination of plural characteristic parameters different from the first combination.

BRIEF DESCRIPTION OF THE DRAWINGS

FIG. 1 is a distribution chart of red blood cells and crystals in a region of fluorescence light intensity-forward scattered light intensity.

FIG. 19 is a flow chart illustrating a procedure of analyzing and displaying process for classification and counting results.

DETAILED DESCRIPTION OF THE PREFERRED EMBODIMENTS

Hereinafter, preferred embodiments of the present invention will be described with reference to the drawings.

[1. Configuration of Sample Analyzer]

Figure 1:
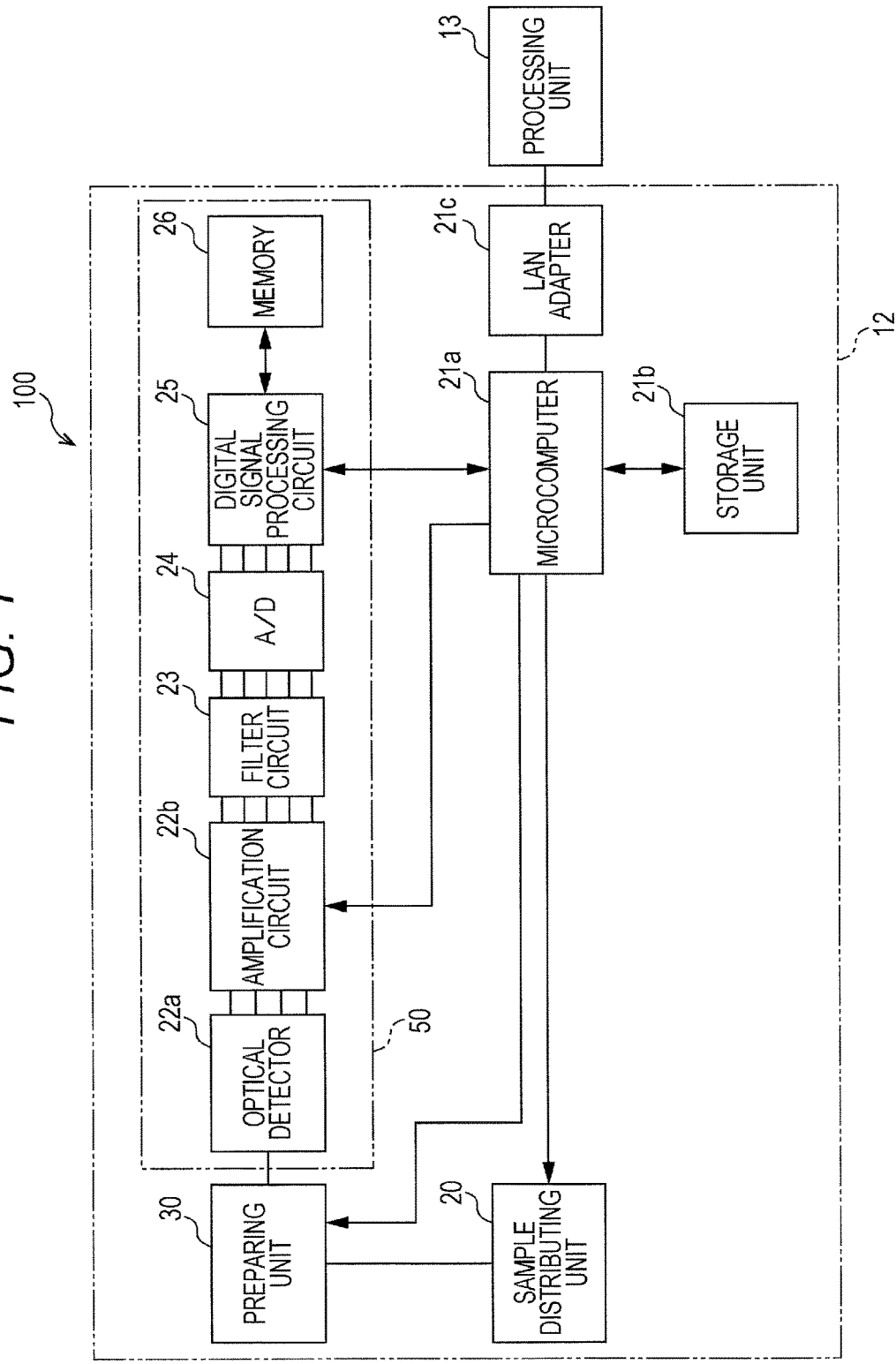
FIG. 1 is a block diagram illustrating a configuration of a sample analyzer.

A sample analyzer 100 illustrated in FIG. 1 analyzes formed elements included in a sample 11. The sample analyzer 100 includes, as main components, a preparing unit 30, a detecting unit 50, and a processing unit 13. The preparing unit 30 mixes the sample 11 with a reagent to prepare a measurement specimen. The detecting unit 50 detects information of the formed elements in the measurement specimen. The processing unit 13 performs a process based on a detection result obtained by the detecting unit 50.

The sample analyzer 100 is operable in either one of a urine analysis mode and a body fluid analysis mode. In the urine analysis mode, the sample analyzer 100 takes a urine sample therein and analyzes urinary formed elements. Examples of the urinary formed elements are red blood cells, white blood cells, epithelial cells, casts, bacteria, fungi (non-sprouted), sperms, and *Trichomonas*.

In the body fluid analysis mode, the sample analyzer 100 takes a body fluid sample therein and analyzes formed elements in the body fluid. Examples of the formed elements in the body fluid are red blood cells, crystals, white blood cells, large cells, fungi, and bacteria. The large cell is a nucleated cell larger than a white blood cell. The large cells are present in the body fluid by, for example, being exfoliated from the inner membrane of coelomic cavity or the peritoneum of an organ. The large cells include epithelial cells, macrophages, and tumor cells.

The body fluid refers to a cell-containing fluid collected from an organism. The body fluid includes spinal fluid, cerebrospinal fluid (CSF), coelomic fluid (pleural fluid, abdominal fluid, pericardial fluid), synovial fluid (synovial fluid: fluid present in synovial bursa and peritenon), eye chamber fluid, and aqueous humor. The body fluid further includes dialysate for peritoneal dialysis (CAPD) and intra-peritoneal wash. According to the general definition, the body fluid includes blood and urine. To distinguish blood and urine from body fluid to be analyzed in the body fluid analysis mode such as cerebrospinal fluid (CSF) and synovial fluid, the term "body fluid" or "body fluid sample" in this embodiment does not include blood and urine. In the claims, the "body fluid" includes blood and urine unless stated otherwise. The "sample" includes blood, urine, and body fluid.

A measuring unit 12 of the sample analyzer 100 includes a sample distributing unit 20, a preparing unit 30, a detecting unit 50, a microcomputer 21a, a storage unit 21b, and a LAN adapter 21c. The measuring unit 12 is connected to a processing unit 13 by way of the LAN adapter 21c.

The detecting unit 50 includes an optical detector 22a, an amplification circuit 22b, a filter circuit 23, an A/D converter 24, a digital signal processing circuit 25, and a memory 26.

Figure 2:
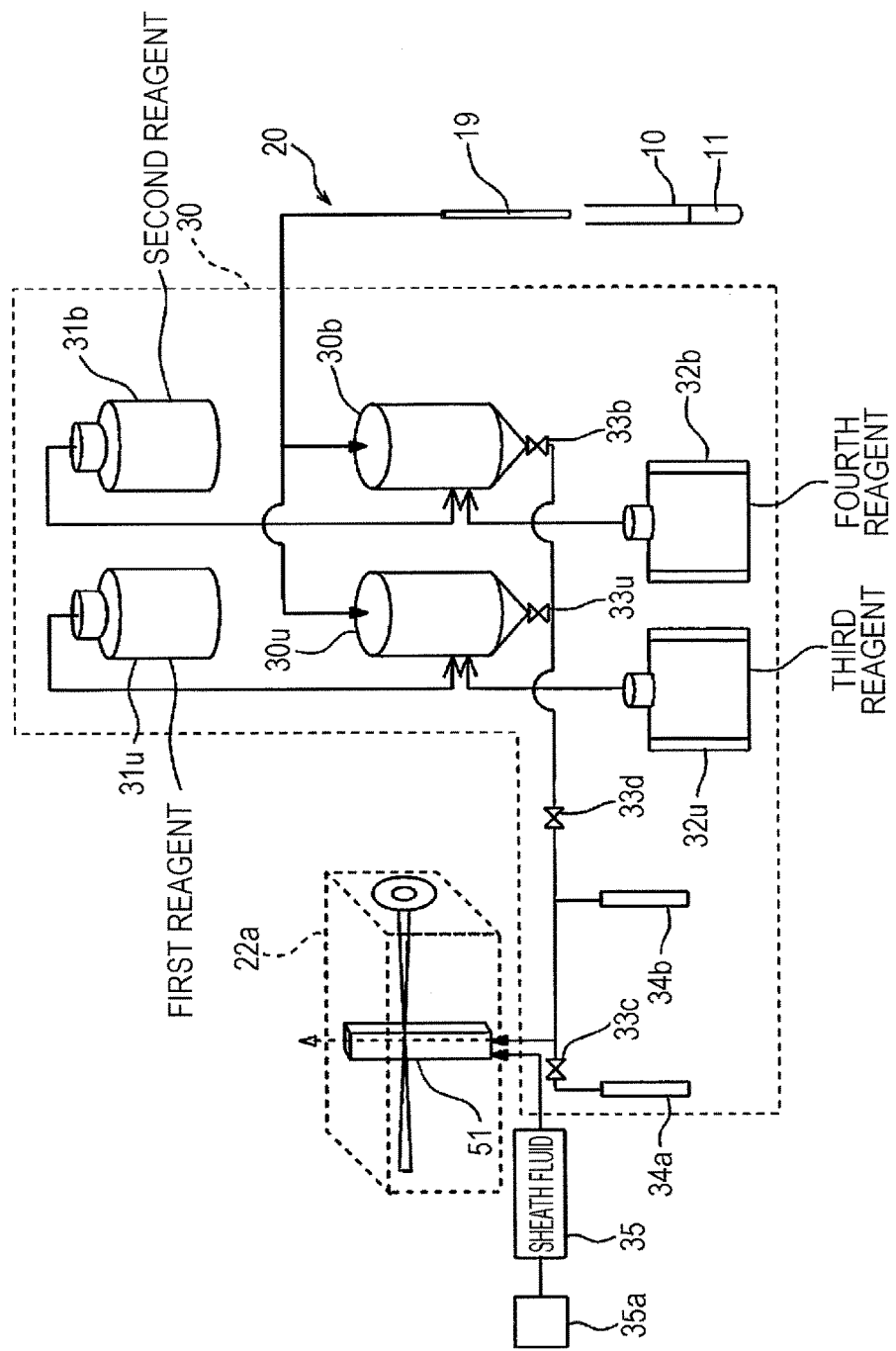
FIG. 2 is a view illustrating a configuration of a preparing unit and an optical detector.

As illustrated in FIG. 2, the preparing unit 30 is connected to the sample distributing unit 20. The preparing unit 30 mixes a reagent with the sample dispensed by the sample distributing unit 20 to prepare a measurement specimen. The sample distributing unit 20 has a suction tube 19 and syringe pumps. The sample distributing unit 20 suctions the sample 11 from a test tube 10 through the suction tube 19 and dispenses the suctioned sample in the preparing unit 30. The preparing unit 30 has a first reaction tank 30u and a second reaction tank 30b. The sample distributing unit 20 distributes a certain quantity of aliquot in each of the first reaction tank 30u and the second reaction tank 30b.

The aliquot in the reaction tank 30u is mixed with a first reagent 31u as a diluent and a third reagent 32u containing dye. The formed elements in the sample are stained with the dye contained in the third reagent 32u. In the urine analysis mode, the specimen prepared in the reaction tank 30$u$ is used as a first measurement specimen for analyzing relatively large urinary formed elements such as red blood cells, white blood cells, epithelial cells, and casts. In the body fluid analysis mode, the specimen prepared in the reaction tank 30$u$ is used as a third measurement specimen for analyzing red blood cells and crystals. Hereinafter, particles lacking nucleic acids in their basic structures, such as red blood cells, casts, and crystals, are referred to as anucleate elements.

The aliquot in the reaction tank 30$b$ is mixed with a second reagent 31$b$ as a diluent, and a fourth reagent 32$b$ containing dye. The second reagent 31$b$ has hemolytic activity. The formed elements in the sample are stained with the dye contained in the fourth reagent 32$b$. In the urine analysis mode, the specimen prepared in the reaction tank 30$b$ is used as a second measurement specimen to analyze urinary bacteria and the like. In the body fluid analysis mode, the specimen prepared in the reaction tank 30$b$ is used as a fourth measurement specimen to analyze white blood cells, large cells, fungi, and bacteria in a body fluid. Hereinafter, particles with nucleic acids in their basic structures, such as white blood cells, large cells, fungi, and bacteria, are referred to as nucleated elements.

A tube extends from the reaction tank 30$u$ to a flow cell 51 in the optical detector 22$a$ of the detecting unit 50, and the measurement specimen prepared in the reaction tank 30$u$ can be introduced into the flow cell 51. An electromagnetic valve 33$u$ is provided at the outlet of the reaction tank 30$u$. Another tube extends from the reaction tank 30$b$, and is coupled to the tube extending from the reaction tank 30$u$ at an intermediate position thereof. The measurement specimen prepared in the reaction tank 30$b$ can be introduced into the flow cell 51. An electromagnetic valve 33$b$ is provided at the outlet of the reaction tank 30$b$.

The tube extending from the reaction tank 30$u$, 30$b$ to the flow cell 51 diverges at a point before it reaches the flow cell 51. The diverging end of the tube is connected to a syringe pump 34$a$. An electromagnetic valve 33$c$ is provided between the syringe pump 34$a$ and the diverging point.

The tube diverges at an intermediate point between the diverging point and a point of connection of the tubes extending from the reaction tanks 30$u$ and 30$b$. The diverging end of the tube is connected to a syringe pump 34$b$. An electromagnetic valve 33$d$ is provided between the connecting point and the diverging point of the tube extending to the syringe pump 34$b$.

The preparing unit 30 has a sheath fluid container 35 to contain a sheath fluid. The sheath fluid container 35 is connected to the flow cell 51 with a tube. A compressor 35$a$ is connected to the sheath fluid container 35. When the compressor 35$a$ is driven, compressed air is introduced into the sheath fluid container 35 to feed the sheath fluid in the sheath fluid container 35 into the flow cell 51.

The measurement specimen is transferred from the reaction tank 30$u$ to the flow cell 51 as described below. A microcomputer 21$a$ opens the electromagnetic valves 33$u$, 33$d$, and 33$c$. In this state, the microcomputer 21$a$ drives the syringe pump 34$a$ to fill a flow path between the electromagnetic valves 33$d$ and 33$c$ with the measurement specimen from the reaction tank 30$u$. The microcomputer 21$a$ closes the electromagnetic valves 33$d$ and 33$c$ and then drives the syringe pump 34$b$ to force out the measurement specimen filling the flow path toward the flow cell 51. Thus, a flow of the measurement specimen enclosed by the sheath fluid is formed within the flow cell 51. When the measurement specimen is transferred from the reaction tank 30$b$, the electromagnetic valve 33$u$ is closed and the electromagnetic valve 33$b$ is opened, so that the flow path is filled with the measurement specimen from the reaction tank 30$b$. Then, similar processing steps follow. The microcomputer 21$a$ controls a force-out rate of the syringe pump 34$b$ to adjust a quantity per unit time of the measurement specimen flowing in the flow cell 51.

Figure 3:
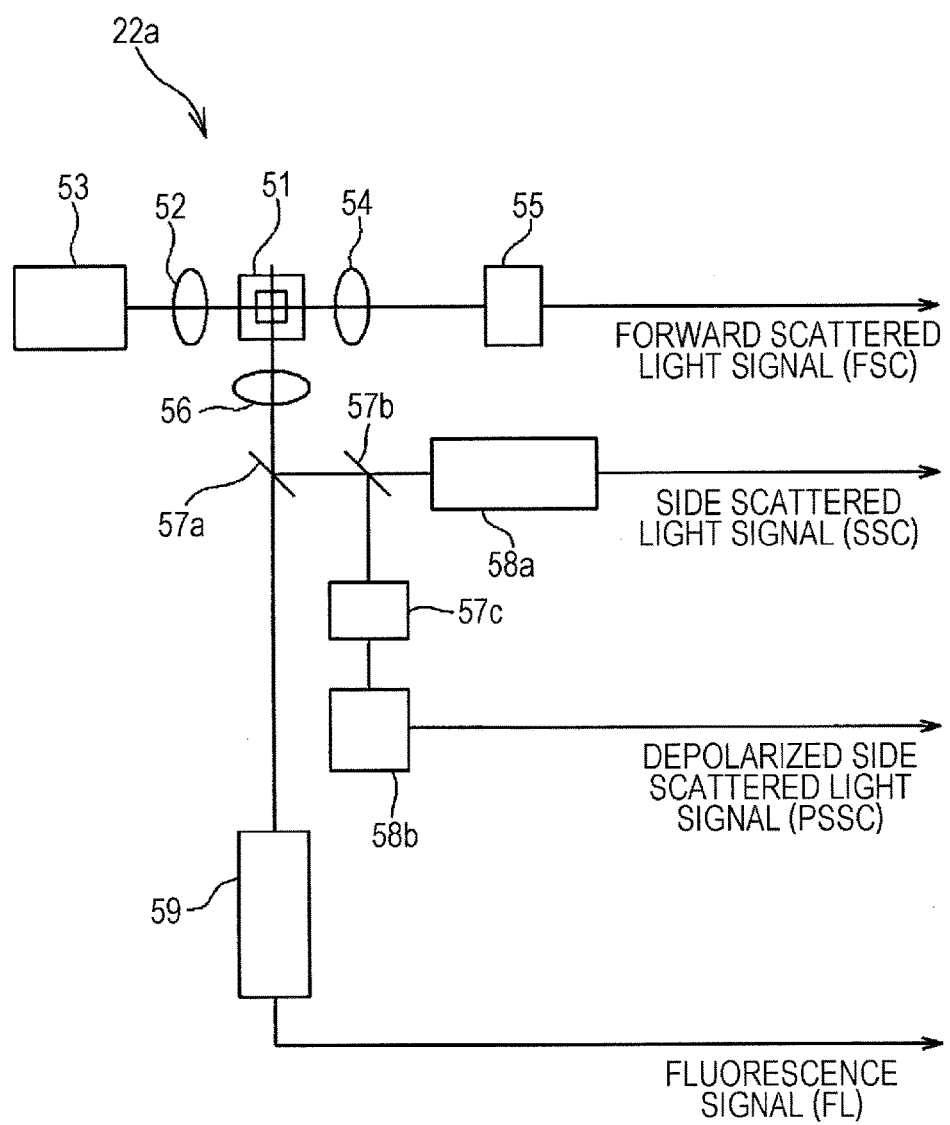
FIG. 3 is a view illustrating the configuration of the optical detector.

As illustrated in FIG. 3, the optical detector 22$a$ has a condenser lens 52 and light collecting lenses 54 and 56. A semiconductor laser light source 53 emits linearly polarized beam in parallel with the specimen flow in the flow cell. The condenser lens 52 condenses the laser beam emitted from the semiconductor laser light source 53 on the flow cell 51. The light collecting lens 54 collects forward scattered light, which is emitted from particles as formed elements in the measurement specimen, on a forward scattered light receiver 55. The forward scattered light receiver 55 detects the forward scattered light. The light collecting lens 56 collects side scattered light and fluorescence light, which are emitted from the formed elements in the measurement specimen, on a dichroic mirror 57$a$. The dichroic mirror 57$a$ reflects the side scattered light toward a half mirror 57$b$, while transmitting therethrough the fluorescence light toward a fluorescence light receiver 59. The fluorescence light receiver 59 detects the fluorescence light.

The half mirror 57$b$ is a non-polarizing mirror. The half mirror 57$b$ splits the side scattered light in halves. The side scattered light transmitting through the half mirror 57$b$ is detected by a side scattered light receiver 58$a$. The side scattered light reflected by the half mirror 57$b$ enters a polarized light filter 57$c$.

The polarized light filter 57$c$ blocks polarized light (light polarized similarly to the light emitted from the semiconductor laser light source 53) in parallel with a flow direction of the measurement specimen flowing in the flow cell 51. The polarized light filter 57$c$ transmits therethrough polarized light vertical to the direction. The side scattered light transmitting through the polarized light filter 57$c$ is hereinafter referred to as "depolarized side scattered light". A depolarized side scattered light receiver 58$b$ detects the depolarized side scattered light.

The forward scattered light receiver 55, side scattered light receiver 58$a$, depolarized side scattered light receiver 58$b$, and fluorescence light receiver 59 respectively convert the received optical signals into electrical signals, and output a forward scattered light signal (FSC), a side scattered light signal (SSC), a depolarized side scattered light signal (PSSC), and a fluorescence signal (FL).

These outputted signals are amplified by a preamplifier, which is not illustrated in the drawings, and then subjected to subsequent processes. By changing drive voltages of the forward scattered light receiver 55, side scattered light receiver 58$a$, depolarized side scattered light receiver 58$b$, and fluorescence light receiver 59, outputs of these receivers may be changed to and from low-sensitivity and high-sensitivity outputs. This sensitivity change is controlled by the microcomputer 21$a$ described later.

According to this embodiment, the forward scattered light receiver 55 is a photo diode, and the side scattered light receiver 58$a$, depolarized side scattered light receiver 58$b$, and fluorescence light receiver 59 are photo photomultiplier tubes. Instead, the forward scattered light receiver 55 may be a photomultiplier tube, and the side scattered light receiver 58$a$, depolarized side scattered light receiver 58$b$, and fluorescence light receiver 59 may be photo diodes. The fluorescence signal (FL) outputted from the fluorescence light receiver 59 is amplified by a preamplifier not illustrated in the drawings and then inputted to two diverging signal channels.

The two signal channels for the fluorescence signal (FL) are connected to the amplification circuit 22b (see FIG. 1) described later. The fluorescence signal inputted to one of the signal channels is amplified in high sensitivity by the amplification circuit 22b. The fluorescence signal inputted to this channel is referred to as a first fluorescence signal (FLH). The fluorescence signal inputted to the other signal channel is amplified in low sensitivity by the amplification circuit 22b. The fluorescence signal inputted to this channel is referred to as a second fluorescence signal (FLL).

Referring to FIG. 1 again, the amplification circuit 22b amplifies the five different signals; FSC, SSC, PSSC, FLH, and FLL, outputted from the optical detector 22a.

The filter circuit 23 applies a filtering process to the signals amplified by the amplification circuit 22b. The A/D converter 24 converts the signals processed by the filter circuit into digital signals. The digital signal processing circuit 25 extracts analysis-use parameters from the respective optical signals. The extracted characteristic parameters are stored as measurement data in the memory 26.

Figure 4A:
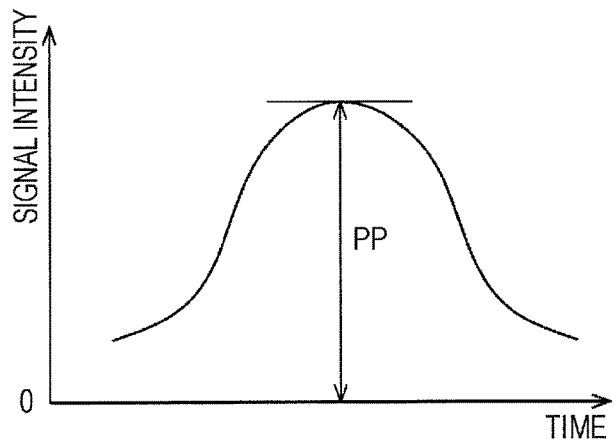
FIG. 4A is a view for explaining the intensity of an optical signal.

The analysis-use parameters extracted by the digital signal processing circuit 25 are described referring to FIG. 4A.

There are three kinds of analysis-use parameters; "intensity", "pulse width", and "pulse area", for the respective optical signals FSC, SSC, PSSC, FLH, and FLL. The intensity is represented by P, the pulse width is represented by W, and the pulse area is represented by A. As described earlier, every time when a particle is passing through the flow cell 51, the electrical signal outputted from each receiver changes in form of a pulse depending on properties of the particle.

Figure 4B:
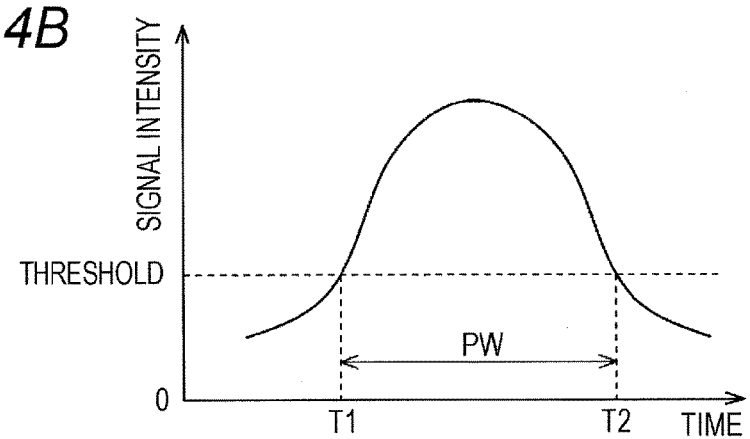
FIG. 4B is a view for explaining the pulse width of the optical signal.
Figure 4C:
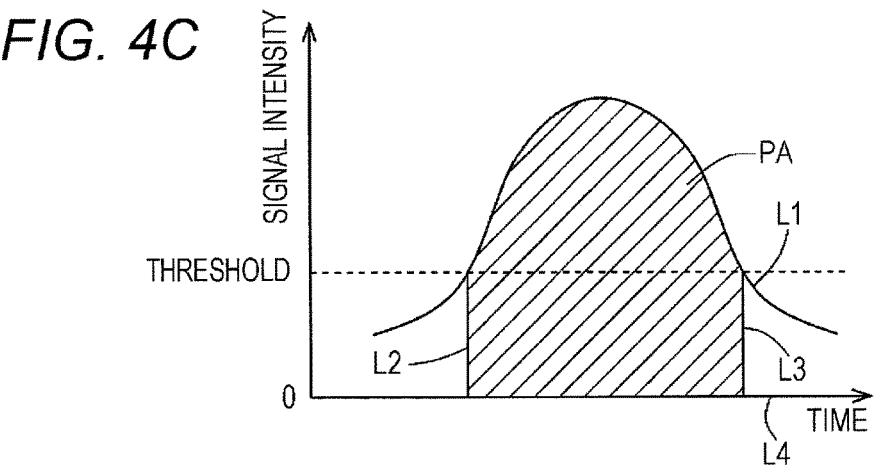
FIG. 4C is a view for explaining the pulse area of the optical signal.

The intensity of an optical signal is obtained as a pulse peak height P as illustrated in FIG. 4A. As illustrated in FIG. 4B, the pulse width of an optical signal is obtained as an interval W between time T1 when a pulse exceeds a predetermined threshold value and time T2 when the pulse falls below the threshold value. As illustrated in FIG. 4C, the pulse area of an optical signal is obtained as the area of a region PA (shaded region in the drawing) defined by lines described below; a pulse waveform line L1 of the optical signal, straight lines L2 and L3 indicating at points in time when the optical signal intensity has a predetermined threshold value on both sides of the pulse, and a straight line L4 on which the optical signal intensity has the value of 0. In other words, the pulse area of the optical signal is obtained as a time integral value of the signal intensity.

The analysis-use parameter extraction method described herein is a non-limiting example. The pulse area is not necessarily the time integral value, and may be an approximate value as far as it reflects an area beneath the time curve of a pulse. For example, the pulse area may be the product of the pulse width and the peak height or may be the area of a triangle obtained from the pulse width and the peak height. To extract the time integral value, the bottom line is not necessarily the straight line indicating the zero intensity and may be appropriately decided. The bottom line may be represented by the predetermined threshold value illustrated in FIG. 4C. Alternatively, a pulse value when the sheath fluid alone is let flown in the flow cell 51 may set as a reference value and used as the bottom line.

Referring to FIG. 2 again, the first to fourth reagents are described in detail. The first reagent 31u is a reagent primarily consisting of a buffer. The first reagent 31u contains an osmotic pressure compensating agent to obtain a stable fluorescence signal without hemolyzing red blood cells. The osmotic pressure of the first reagent 31u is regulated to stay in a range of pressures suitable for classifying and measuring the sample; 100 to 600 mOsm/kg. The first reagent 31u does not have hemolytic activity for urinary red blood cells.

Unlike the first reagent 31u, the second reagent 31b has hemolytic activity. One motive for using such a reagent is to facilitate passage of the fourth reagent 32b through cell membranes of fungi and bacteria, thereby accelerating dye-staining. Another motive is to promote contraction of impurities including mucosae and red blood cell fragments. The second reagent 31b contains a surfactant to acquire hemolytic activity. The surfactant may be selected from anionic, nonionic, and/or cationic surfactants. A particularly suitable example is a cationic surfactant. Because of the surfactant's ability to damage the cell membranes of fungi and bacteria, nucleic acids of nucleated elements, such as fungi and bacteria, may be more efficiently stained with the dye contained in the fourth reagent 32b. This quickened staining treatment facilitates the measurements of fungi and bacteria.

Instead of using the surfactant, the second reagent 31b may be adjusted to be acidic or to low pH to acquire hemolytic activity. The low pH is more specifically pH lower than that of the first reagent 31u. In contrast to the first reagent 31u with neutrality or weak acidity to weak alkaline, the second reagent 31b has acidity or strong acidity. In contrast to the first reagent 31u with pH of 6.0 to 8.0, the second reagent 31b has lower pH, preferably 2.0 to 6.0. Optionally, the surfactant-containing second reagent 31b may be further subjected to adjustment to low pH. The second reagent 31b may acquire hemolytic activity by having its osmotic pressure reduced to be lower than that of the first reagent 31u.

The first reagent 31u contains no surfactant. The first reagent 31u may optionally contain a surfactant, in which case a surfactant to be added and its concentration need to well-managed to avoid hemolysis of red blood cells. Preferably, the first reagent 31u does not contain the same surfactant as the second reagent 31b, or may contain the same surfactant at a lower concentration than the second reagent 31b.

The second reagent 32u is a staining reagent for staining anucleate elements. The third reagent 32u contains a fluorescent dye more likely to bond to lipid and protein of cell membranes than nucleic acids. Such a dye is preferably any one of cyanine-based, styryl-based, and acridine-based dyes not affecting red blood cells in shape. The dye for staining anucleate formed elements is preferably selected from fat-soluble carbocyanine dyes. Particularly preferable examples are indocarbocyanine dyes and oxacarbocyanine dyes.

Specific examples of the indocarbocyanine dyes are: DiI(1,1'-dioctadecyl-3,3,3',3'-tetramethylindocarbocyanine perchlorate); DiD(1,1'-dioctadecyl-3,3,3',3'-tetramethylindodicarbocyanine); and DiR(1,1'-dioctadecyltetramethyl indotricarbocyanine Iodide). Specific examples of the oxacarbocyanine dyes are: DiOC2(3)(3,3'-diethyloxacarbocyanine iodide); DiOC3(3)(3,3-Dipropyloxacarbocyanine iodide); DiOC4(3) (3,3'-Dibutyloxacarbocyanine iodide); and DiOC5(3)(3,3-Dipentyloxacarbocyanine iodide). A particularly preferable dye for staining the anucleate elements is DiOC3(3)3,3-Dipropyloxacarbocyanine iodide.

The fourth reagent 32b is a staining reagent for staining nucleated elements. The fourth reagent 32b contains a fluorescent dye more likely to bond to nucleic acids than lipid or protein. The fourth reagent 32b more particularly contains an intercalating dye for specifically staining nucleic acids or a dye that bonds to minor grooves.

Examples of the intercalating dye are known dyes such as cyanine-based, acridine-based, and phenanthridium-based dyes. Examples of the cyanine-based intercalating dye are SYBR Green I, and Thiazole orange. An example of the acridine-based intercalating dyes is Acridinorange. Examples of the phenanthridium-based intercalating dye are propidium Iodide, and Ethidium bromide. Examples of the minor groove-bonding dye are DAPI, and Hoechst. Examples of the minor groove-bonding Hoechet are Hoechst 33342, and Hoechst 33258. According to this embodiment, the cyanine-based intercalating dyes are preferably used, among which SYBR GreenI, and Thiazole orange are particularly preferable.

In the urine analysis mode, a first measurement specimen containing red blood cells retaining their shapes and stained cell membranes, and a second measurement specimen containing stained nucleic acids of nucleated elements and hemolyzed red blood cells are prepared from one urine sample. The first measurement specimen is used to measure urinary red blood cells, casts, and crystals. The second measurement specimen is used to measure urinary white blood cells, epithelial cells, atypical cells, fungi, sperms, *Trichomonas*, and bacteria. Conventionally, high-accuracy classification is a long-awaited technique to allow for distinction between blood cells and fungi that are alike in size. According to this embodiment wherein fungi is measured by using the second measurement specimen containing hemolyzed red blood cells, fungi may be very accurately measured and counted without being affected by red blood cells.

In the body fluid analysis mode, a third measurement specimen for measuring red blood cells and crystals in body fluid, and a fourth measurement specimen for measuring white blood cells, large cells, fungi, and bacteria in body fluid are prepared from one body fluid sample. The third measurement specimen is used to measure red blood cells and crystals in body fluid. The fourth measurement specimen is used to measure white blood cells, large cells, fungi, and bacteria in body fluid. By preparing the fourth measurement specimen containing hemolyzed red blood cells, as with the urine analysis mode, fungi may be accurately measured without being affected by red blood cells.

The first reagent 31*u* and the third reagent 32*u* are both used to measure urinary formed elements in the urine analysis mode and to measure red blood cells in body fluid in the body fluid analysis mode. The second reagent 31*b* and the fourth reagent 32*b* are both used to measure bacteria in the urine analysis mode and to measure white blood cells, large cells, fungi, and bacteria in body fluid in the body fluid analysis mode. Using these reagents for the urine analysis mode and the body fluid analysis mode makes it unnecessary to prepare different reagents for dedicated purposes.

Figure 5:
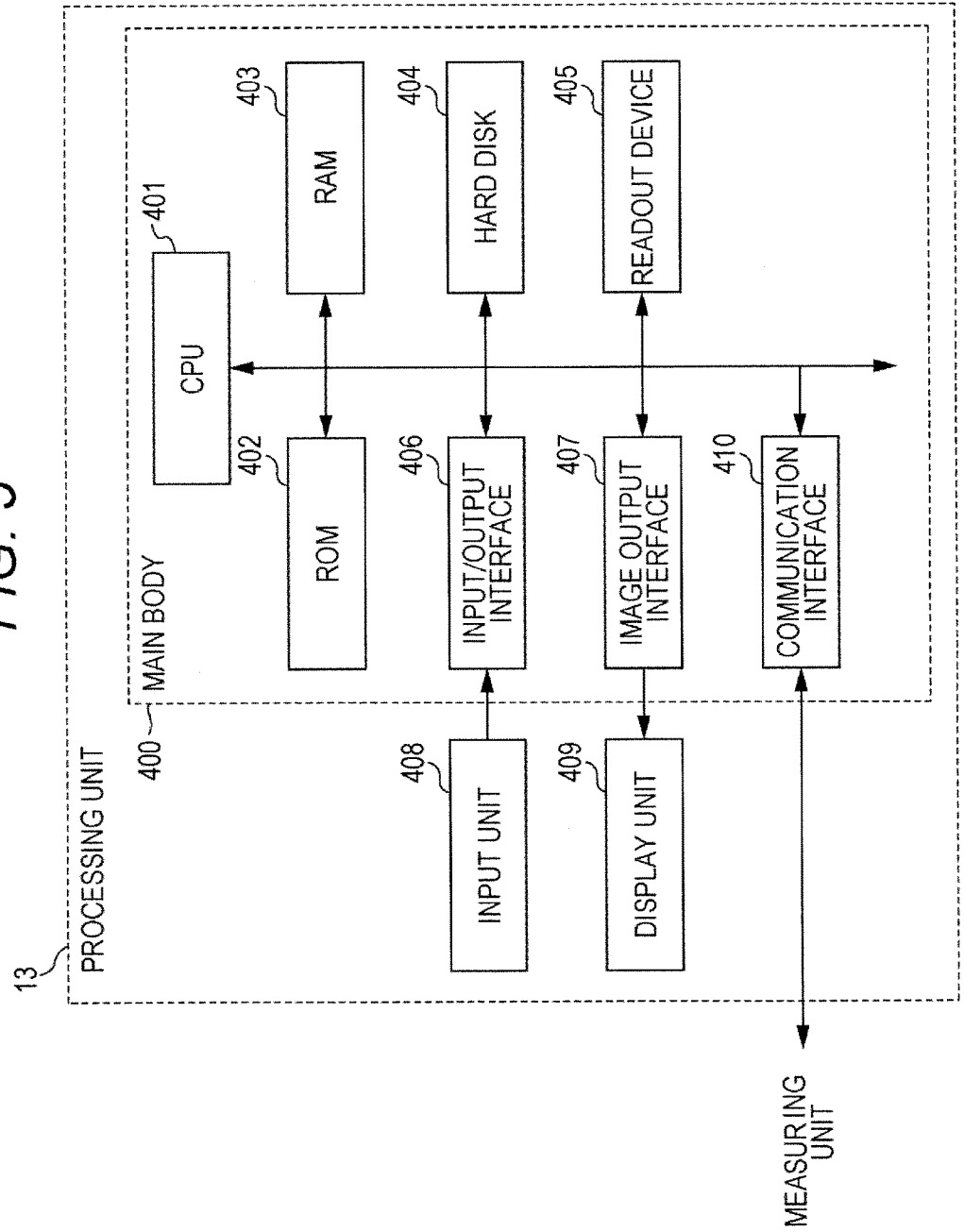
FIG. 5 is a block diagram illustrating a configuration of a processing unit.

FIG. 5 is a block diagram illustrating structural characteristics of the processing unit 13. The processing unit 13 includes a personal computer. The processing unit 13 has a body 400, an input unit 408, and a display unit 409. The body 400 has a CPU 401, a ROM 402, a RAM 403, a hard disc 404, a readout unit 405, an input/output interface 406, an image output interface 407, and a communication interface 410.

The CPU 401 runs computer programs stored in the ROM 402 and loaded in the RAM 403. The RAM 403 is used to read out the computer programs stored in the ROM 402 and the hard disc 404. The RAM 403 may also be used as a workspace for the CPU 401 when these computer programs are run.

In the hard disc 404 are installed and stored different computer programs and data used to run these computer programs. The programs installed therein include an operating system and application programs. The application programs include a computer program for analyzing measurement data provided by the measuring unit 12 and output an analysis result.

The readout unit 405 includes a CD drive or a DVD drive. The readout unit 405 is operable to read out the computer programs and data recorded on recording media. The input unit 408 including a mouse and a keyboard is connected to the input/output interface 406. A user, by manipulating the input unit 408, may input data to the processing unit 13. The image output interface 407 is connected to the display unit 409 including a liquid crystal panel. The image output interface 407 outputs image signals in accordance with image data to the display unit 409. The display unit 409 displays images based on the inputted image signals. The processing unit 13 is connected to the measuring unit 12 by way of the communication interface 410. The data is transmitted to and received from the measuring unit 12 through the communication interface 410.

[2. Operation of Sample Analyzer]
[Analysis Mode Setting]

When the sample analyzer 100 is activated, the CPU 401 of the processing unit 13 is programmed to be in the urine analysis mode by default. When a measurement carry-out instruction (S501 in FIG. 6 described later) is received by the CPU 401 in the urine analysis mode, the CPU 401 prompts the microcomputer 21*a* of the measuring unit 12 to perform a sample measuring operation to analyze urine. Then, measurement data obtained by the urine-analysis sample measuring is analyzed by the CPU 401 of the processing unit 13, so that particles are classified and counted based on counting target items for the urine analysis mode.

The CPU 401 of the processing unit 13 may receive a mode change instruction to change the operation mode to and from the urine analysis mode and the body fluid analysis mode. The CPU 401 that received the mode change instruction is programmed to be in the body fluid analysis mode. The CPU 401 prompts the microcomputer 21*a* of the measuring unit 12 to carry out pre-sequence. The pre-sequence refers to background check performed by measuring a sheath fluid as a blank specimen containing no cell. In the absence of any problem with the background confirmed by the pre-sequence, the CPU 401 is ready to receive the measurement carry-out instruction. When the CPU 401 in the body fluid analysis mode receives the measurement carry-out instruction (S501 in FIG. 6 described later), the CPU 401 prompts the microcomputer 21*a* of the measuring unit 12 to carry out a measurement sequence to analyze body fluid. Then, measurement data obtained by the body fluid-analysis sample measuring is analyzed by the CPU 401 of the processing unit 13, so that particles are classified and counted based on counting target items for the body fluid analysis mode.

[Sample Measuring Operation]

Figure 6:
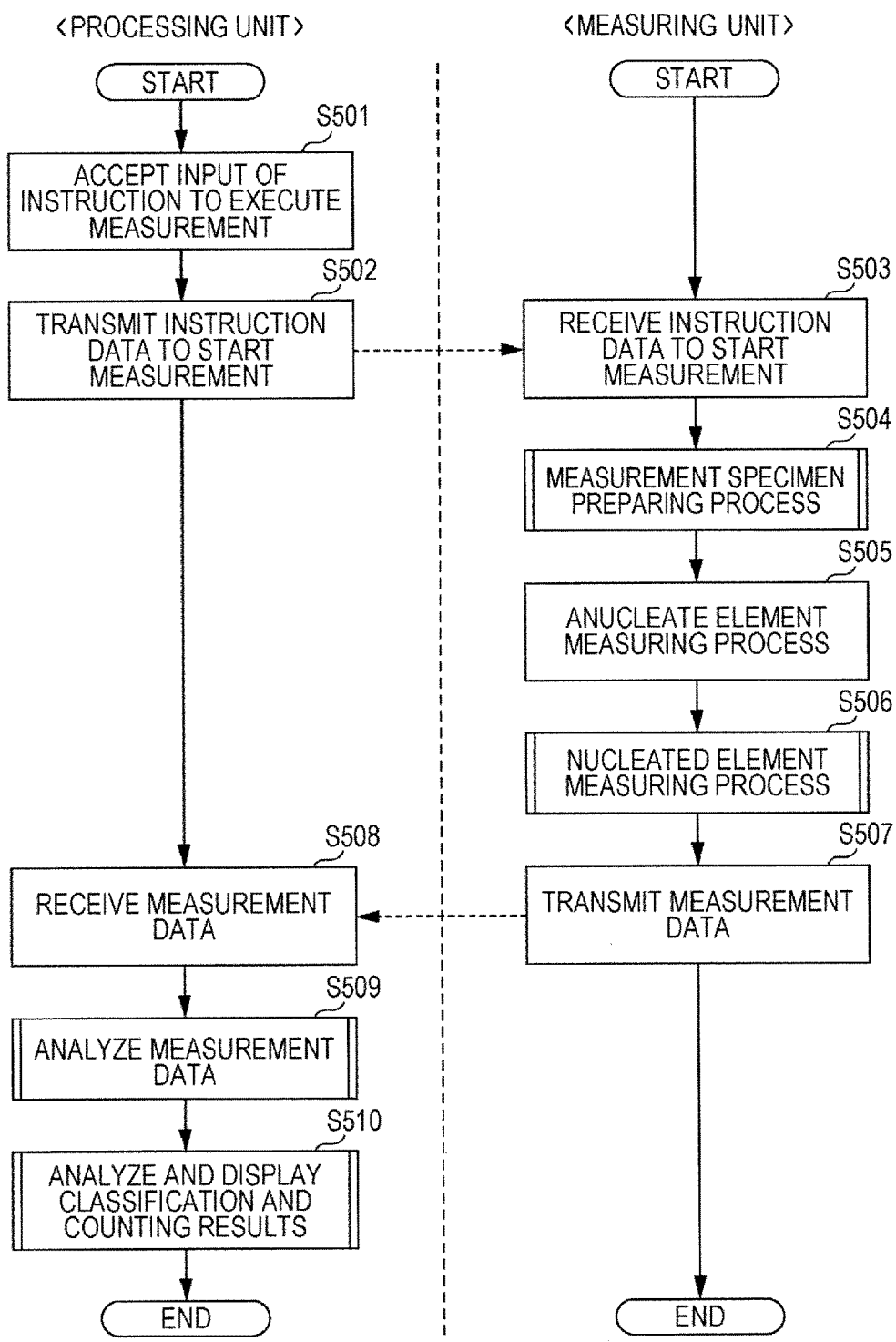
FIG. 6 is a flow chart illustrating a procedure of a sample measuring process in a body fluid analysis mode.

Referring to FIG. 6, the sample measuring operation is described. The sample measuring operation in the urine analysis mode and the sample measuring operation in the body fluid analysis mode basically follows the same sequence. Hereinafter, the sample measuring operations in the two modes are described referring to the same flow chart.

Figure 7:
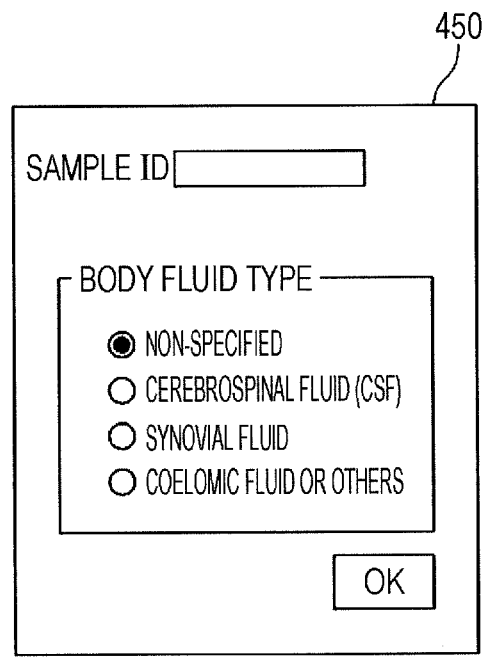
FIG. 7 shows an information input screen for input of different types of body fluid samples.

In step S501 of FIG. 6, the measurement carry-out instruction is inputted to the input unit 408 of the processing unit 13. In the body fluid analysis mode, an information input screen 450 illustrated in FIG. 7 is displayed on the display unit 409 of the processing unit 13. A user may input a sample ID and the type of a target body fluid sample on the information input screen. In the body fluid analysis mode, body fluid sample options displayed on the screen are "cerebrospinal fluid", "coelomic fluid", "synovial fluid and others", and "not specified". By pressing one of radio buttons displayed next to the respective options, the user may input the type of a body fluid sample to be measured. There may be emergency cases that urgently request the measurement results of body fluid samples. To avoid any incorrect inputs in such time-sensitive cases, "not specified" may be selected as a default option, so that the measuring operation may start without specifying the type of a body fluid sample. When the user selects one of the body fluid sample options and presses the OK button, the CPU 401 receives the measurement carry-out instruction.

In step S502, the CPU 401, in response to the instruction, transmits instruction data to the measuring unit 12, instructing the measuring operation to start. In step S503, when the measuring unit 12 receives the instruction data, the microcomputer 21a carries out S504; a measurement specimen preparing step, and S506; a nucleated element measuring step.

Figure 8:
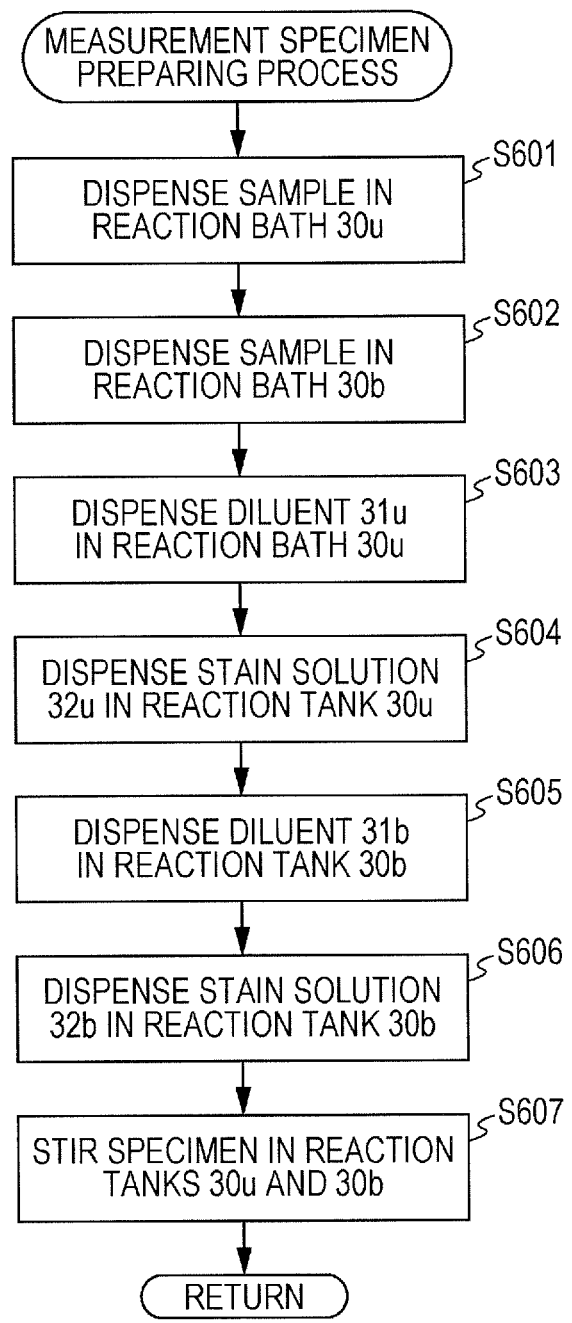
FIG. 8 is a flow chart illustrating a procedure of a body fluid measurement specimen preparing process.

As illustrated in FIG. 8, in sub-steps S601 and S602 of the measurement specimen preparing step S504, the microcomputer 21a controls the preparing unit 30 to have a predetermined quantity of the sample 11 in the test tube 10 be suctioned by the suction tube 19. The microcomputer 21a further prompts the suction tube 19 to dispense the sample in a predetermined quantity in each of the reaction tanks 30u and 30b.

In sub-steps S603 and S604, a certain quantity of the sample 11 and predetermined quantities of the first reagent (diluent) 31u and third reagent (staining solution) 32u are dispensed in the reaction tank 30u. Similarly, in sub-step S605 and S606, a certain quantity of the sample 11 and predetermined quantities of the second reagent (diluent) 31b and fourth reagent (staining solution) 32b are dispensed in the reaction tank 30b.

The reaction tank 30u and 30b are heated by heaters not illustrated in the drawings to stay at predetermined temperatures. In step S607, the specimens are heated and agitated in the tanks respectively by propeller-like agitators (not illustrated in the drawings), and the respective specimens are accordingly prepared. In the urine analysis mode, the first measurement specimen for measuring anucleate elements is prepared in the reaction tank 30u, and the second measurement specimen for measuring nucleated elements is prepared in the reaction tank 30b. In the body fluid analysis mode, the third measurement specimen for measuring anucleate elements is prepared in the reaction tank 30u, and the fourth measurement specimen for measuring nucleated elements is prepared in the reaction tank 30b. When sub-step S607 is over, the microcomputer 21a returns to the main routine.

Referring to FIG. 6 again, in the anucleate element measuring step S505, the microcomputer 21a feeds compressed air from the compressor 35a into the sheath fluid container 35, thereby forcing the sheath fluid out into the flow cell 51. Along with the ongoing feed of the sheath fluid to the flow cell 51, the microcomputer 21a drives the syringe pump 34b to feed the third measurement specimen from the reaction tank 30u into the flow cell 51.

According to a preferred embodiment, a force-out quantity per unit time of the syringe pump 34b may differ between the urine analysis mode and the body fluid analysis mode. Preferably, the force-out quantity per unit time during the body fluid analysis mode may be ⅛ of the force-out quantity during the urine analysis mode.

Figure 9A:
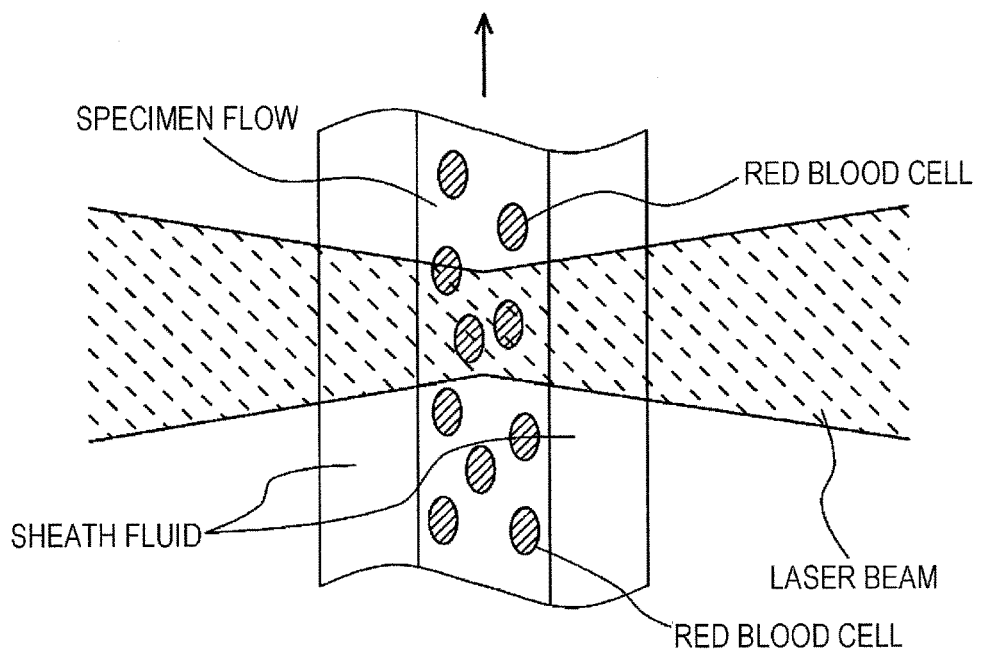
FIG. 9A is a schematic view of a sheath flow.
Figure 9B:
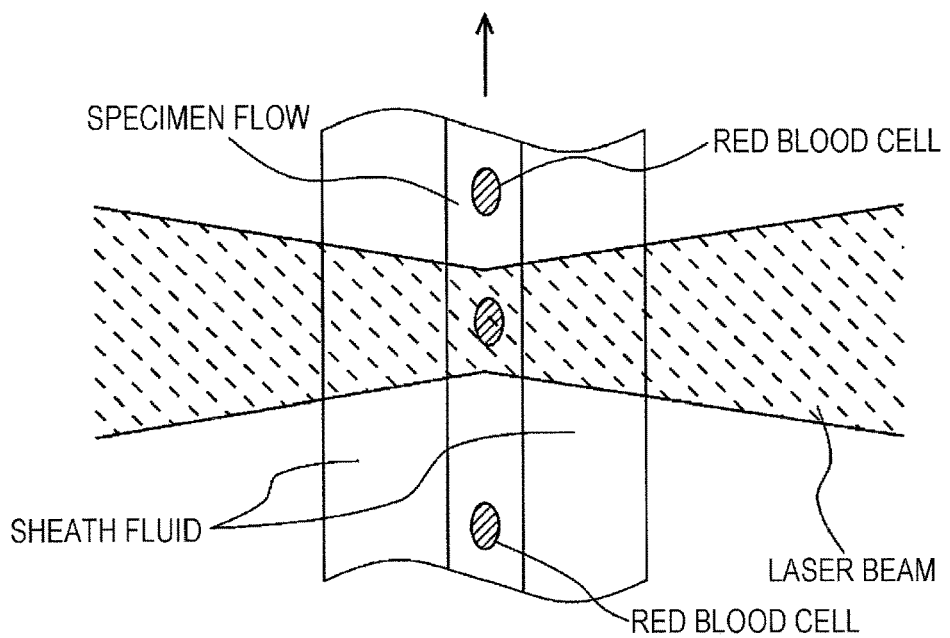
FIG. 9B is a schematic view of a sheath flow.

Often, body fluid samples may contain red blood cells at higher concentrations than urine samples. As illustrated in FIG. 9A, if the measurement specimen prepared from body fluid is overly forced out per unit time, multiple red blood cells may pass through the laser beam at once. As illustrated in FIG. 9B, reduction of the force-out quantity per unit time results in a diametrically smaller specimen flow. This may allow each one of red blood cells to pass through the laser beam separately, leading to a higher counting accuracy.

The microcomputer 21a prompts the laser light source 53 to emit laser beam. Then, forward scattered light, fluorescence light, side scattered light, and depolarized side scattered light are accordingly emitted from particles in the third measurement specimen. The forward scattered light, fluorescence light, side scattered light, and depolarized side scattered light are respectively received by the forward scattered light receiver 55, fluorescence light receiver 59, side scattered light receiver 58a, and depolarized side scattered light receiver 58b. These lights are then converted into five different optical signals; FSC, FLH, FLL, SSC, and PSSC.

The optical signals outputted from the optical detector 22a are amplified by the amplification circuit 22b. The amplified optical signals are then subjected to the filtering process by the filter circuit 23, and converted into digital signals by the A/D converter 24. The digital signal processing circuit 25 extracts analysis-use parameters from the optical signals. The extracted characteristic parameters are stored as measurement data in the memory 26.

In the nucleated element measuring step S506, as with the anucleate element measuring step, the microcomputer 21a drives the compressor 35a and the syringe pump 34b to introduce the fourth measurement specimen from the reaction tank 30b into the flow cell 51 containing the sheath fluid. When the laser beam is emitted from the laser light source 53 by the microcomputer 21a, five different optical signals emitted from particles in the fourth measurement specimen are detected. Then, analysis-use parameters of the optical signals are extracted and stored in the memory 26.

In a given period of time after the fourth measurement specimen starts to be supplied, the microcomputer 21a sets the light sensitivities of the forward scattered light receiver 55, side scattered light receiver 58a, and fluorescence light receiver 59 to the high sensitivity level, specifically, their gains are set to values five times larger. This is because bacteria are smaller than the other nucleated cells, and their fluorescence amount is less than the other nucleated cells. The high sensitivity enables high-accuracy detection of trace amounts of light emitted from bacteria.

For a predetermined period of time subsequent to the light sensitivity change, the sheath fluid and the fourth measurement specimen continue to be introduced into the flow cell 51, and the laser beam irradiation continues as well. Then, five different optical signals emitted from the particles of the fourth measurement specimen are detected. Then, analysis-use parameters of the optical signals are extracted and stored in the memory 26.

In step S507, the microcomputer 21a transmits the measurement data obtained in the anucleate element measuring step and the nucleated element measuring step to the data processing unit 13. Then, the microcomputer 21a ends the operation.

In step S509, the CPU 401 analyzes the measurement data. Then, the CPU 401 generates a sample analysis result and stores the analysis result in the hard disc 404. In step S510, the CPU 401 displays the analysis result.

Figure 10:
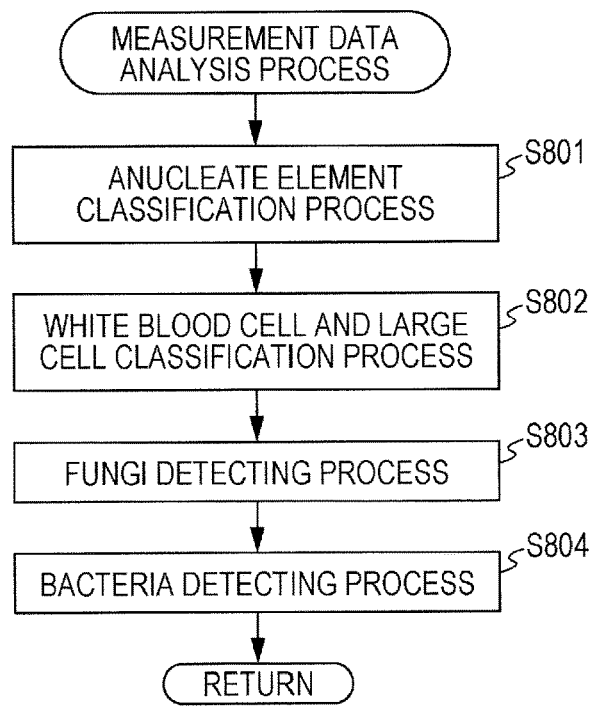
FIG. 10 is a flow chart illustrating a procedure of a measurement data analysis process.

FIG. 10 is a flow chart of the subroutine of the analyzing step S509. The CPU 401 carries out step S801 for classifying anucleate elements, step S802 for classifying white blood cells and large cells, step S803 for detecting fungi, and step S804 for detecting bacteria.

Figure 11:
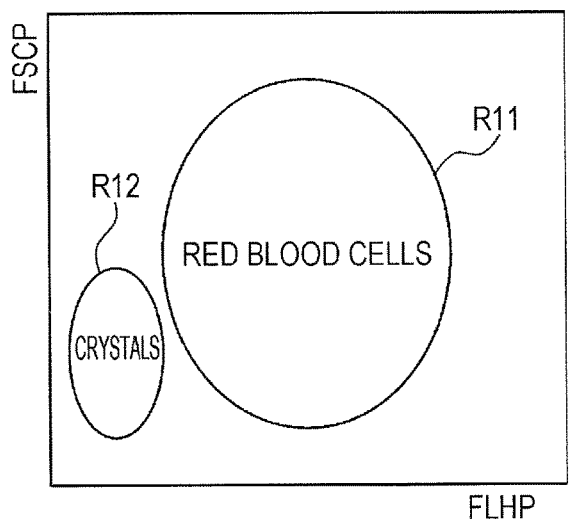

In the anucleate element classifying step S801 during the urine analysis mode, the CPU 401 distinguishes between red blood cells and crystals by using FSC and FLH obtained from the first measurement specimen. The CPU 401 further counts them. FIG. 11 is a distribution chart of red blood cells and crystals. In FIG. 1, the lateral axis represents the intensity of FLH (FLHP), and the vertical axis represents the intensity of FSC (FSCP). As illustrated in FIG. 11, distinction in FLHP is observed between a red blood cell distributed region RI 1 and a crystal distributed region R12. This distinction results from the fact that red blood cells and crystals differ in stainability. Therefore, red blood cells and crystals may be classified based on FLHP.

In the anucleate element classifying step S801 during the body fluid analysis mode, as with the urine analysis mode, red blood cells and crystals are classified and counted by using FSC and FLH obtained from the third measurement specimen.

In the anucleate element classifying step S801, particles present in the region R11 of FIG. 1 are detected and counted as red blood cells, and particles present in the region R12 of FIG. 11 are detected and counted as crystals.

In the anucleate element classifying step S801 during the urine analysis mode, casts are then counted by using FLLW and FLLA obtained from the first measurement specimen. During the body fluid analysis mode, casts, which are not found in body fluid, are not counted.

In the white blood cell and large cell classifying step S802 during the urine analysis mode, white blood cells, epithelial cells, and atypical cells are detected and counted by using FSC and FLL obtained from the second measurement specimen before the sensitivity change. The scattered light signal reflects a particle size. The fluorescence signal reflects the nucleic acid amount of a particle. The white blood cell, epithelial cell, and atypical cell contain has larger nucleic acid amounts than the fungus and bacterium, and their fluorescence amounts are accordingly relatively large. To detect these cells, therefore, the second fluorescence signal (FLL) obtained in low sensitivity is used as the fluorescence signal (FL).

Figure 12A:
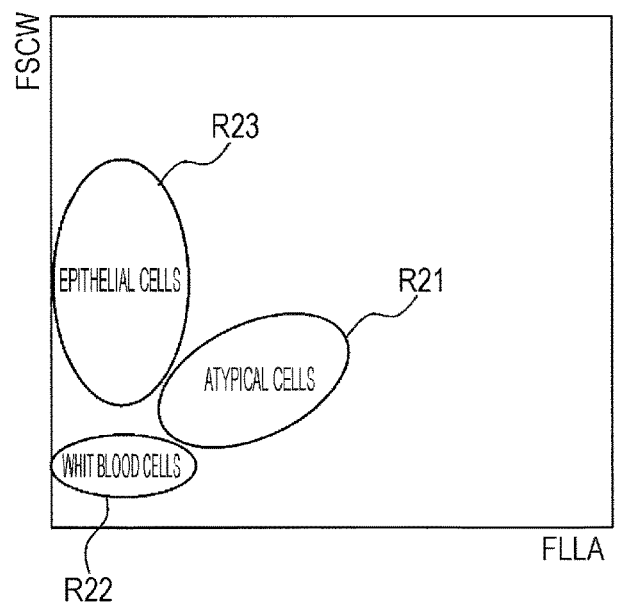
FIG. 12A is a distribution chart of white blood cells, atypical cells, and epithelial cells in a region of fluorescence pulse area-forward scattered light pulse width.

As illustrated in FIG. 12A, white blood cells, epithelial cells, and atypical cells are distributed in FLLA-FSC space. The lateral axis of FIG. 12A represents the pulse area of FLL (FLLA). The vertical axis of FIG. 12A represents the pulse area of FSC (FSCW). As illustrated in FIG. 12A, distinction in FLLA is observed between atypical cells, and white blood cells and epithelial cells. The distinction results from hardly different nucleic acid amounts of the white blood cell and epithelial cell, whereas the atypical cell has a larger nucleic acid amount than the white blood cell and epithelial cell.

Figure 12B:
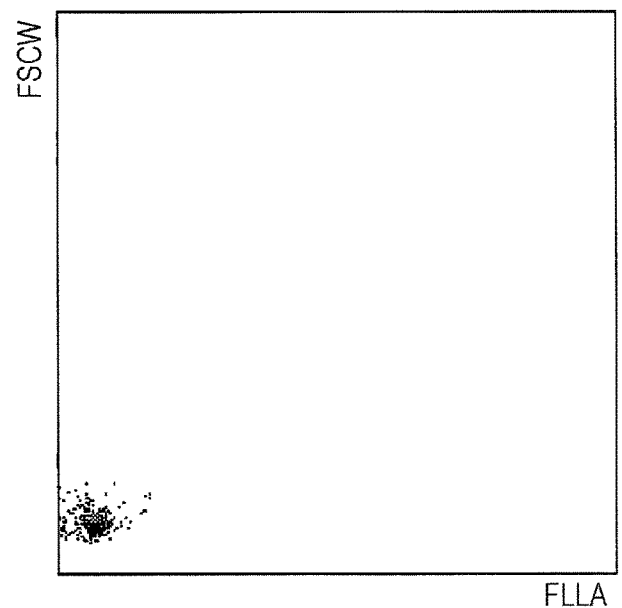
FIG. 12B is a scattergram illustrating an example of a detection result on white blood cells.

In FSCW, distinction is observed between white blood cells and epithelial cells because epithelial cells categorized as large cells are larger in size than white blood cells. Therefore, white blood cells, large cells (epithelial cells), and atypical cells are classified based on FLLA and FSCW. In the white blood cell and large cell classifying step S802, particles present in the region R21 of FIG. 12A are detected and counted as atypical cells. FIG. 12B illustrates an exemplified detection result of white blood cells. In FIG. 12A, particles present in the region R22 are detected and counted as white blood cells, and particles present in the region R23 are detected and counted as epithelial cells.

In the white blood cell and large cell classifying step S802 during the body fluid analysis mode, as with the urine analysis mode, white blood cells, epithelial cells, and atypical cells are detected and counted by using the FSC and FLH obtained from the fourth measurement specimen. To count these cells, epithelial cells and atypical cells are collectively counted as large cells (LC). In addition to epithelial cells, large cells to be counted may include other nucleated cells such as tumor cells.

The body fluid sample contains, in addition to white blood cells, other relatively large cells. Specifically, the body fluid sample contains nucleated cells larger than white blood cells, for example, epithelial cells or tumor cells. To combine the scattered light signal pulse width (FSCW) and the fluorescence signal pulse area (FLLA) is suitable for detection of large nucleated cells. In this manner, white blood cells and large cells in body fluid may be both very accurately counted.

In the white blood cell and large cell classifying step S802 during the body fluid analysis mode, white blood cells and epithelial cells are counted. In addition to that, nucleated cells in total including white blood cells, epithelial cells (large cells), and atypical cells are further counted and obtained as a total nucleated cell count (TNC).

The particles counted in the body fluid analysis mode include the same ones as in the urine analysis mode, such as red blood cells and white blood cells, but may further include elements not counted in the urine analysis mode such as large cells and nucleated cells in total. On the other hand, casts, for example, not counted in the body fluid analysis mode are counted in the urine analysis mode. Thus, the sample analyzer 100 classifies and counts the elements based on counting target items respectively specified for the urine analysis mode and the body fluid analysis mode.

Supposing that the fourth measurement specimen contains bacteria or fungi, the regions R22 and R23 illustrated in FIG. 12A are useful for distinguishing white blood cells and epithelial cells from bacteria and fungi much smaller than white blood cells. Thus, the total nucleated cell count (TNC) may be obtained as the total count of white blood cells and nucleated cells larger than white blood cells that are distinguished from fungi or bacteria.

In the white blood cell and large cell classifying step S802 during the body fluid analysis mode, white blood cells detected as being present in the region R22 (see FIG. 12B) are further classified. More specifically, white blood cells are classified in two categories; mononuclear white blood cells (WBC (MN)), and polymorphonuclear white blood cells (WBC (PMN)). It is not particularly limited what and how many categories should be used to classify white blood cells. For example, white blood cells may be classified in five different categories; lymphocyte, monocyte, neutrophile, acidocyte, and basocyte. Because of a small count of white blood cells in body fluid, more classification categories may result in a fewer-than-expected count of white blood cells in each category. This possibly leads to poor accuracy in classifying these cells. Therefore, white blood cells may be preferably classified in two categories.

The classification of white blood cells makes use of the forward scattered light signal (FSC) and the side scattered light signal (SSC) obtained from the fourth measurement specimen before the sensitivity change. As the result of classifying white blood cells, mononuclear white blood cells and polymorphonuclear white blood cells are detected to obtain a mononuclear WBC count (MN#) and a polymorphonuclear WBC count (PMN#). Based on the proportion of these counts, a mononuclear WBC ratio (MN %) and a polymorphonuclear WBC ratio (PMN %) are calculated.

Figure 13:
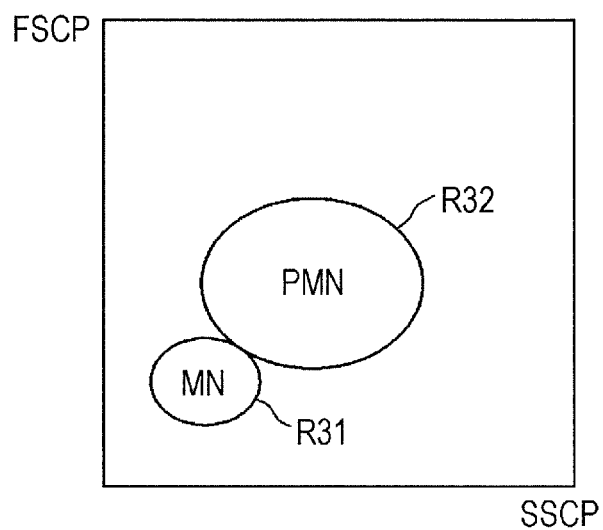
FIG. 13 is a distribution chart of mononuclear leukocytes and polymorphonuclear leukocytes in a region of side scattered light intensity-forward scattered light intensity.

As illustrated in FIG. 13, mononuclear white blood cells and polymorphonuclear white blood cells are distributed in SSCP-FSCP space. In FIG. 13, the lateral axis represents the intensity of the side scattered light signal (SSCP), and the vertical axis represents the intensity of the forward scattered light signal (FSCP). In place of these signals, intensities of the fluorescence signal and the side scattered light signal may be employed to classify white blood cells.

Figure 14A:
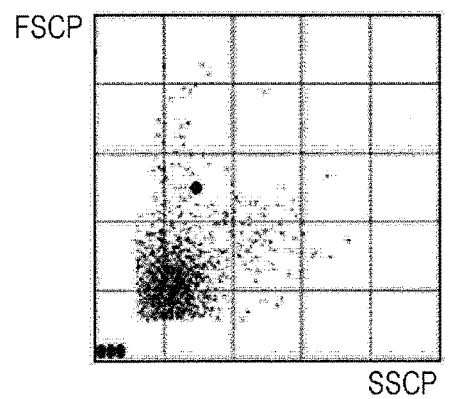
FIG. 14A is a scattergram illustrating an example of a detection result on mononuclear leukocytes and polymorphonuclear leukocytes.
Figure 14B:
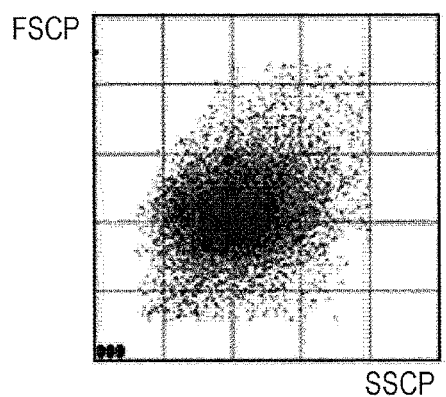
FIG. 14B is a scattergram illustrating an example of the detection result on mononuclear leukocytes and polymorphonuclear leukocytes.
Figure 14C:
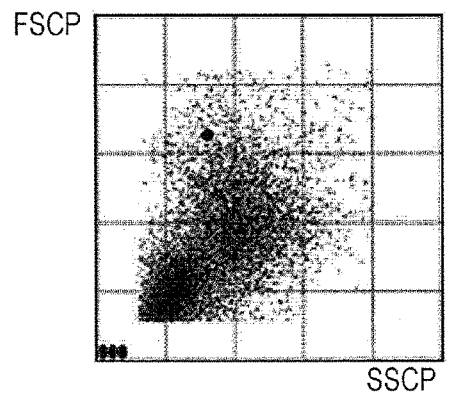
FIG. 14C is a scattergram illustrating an example of the detection result on mononuclear leukocytes and polymorphonuclear leukocytes.

FIGS. 14A to 14C illustrate detection results for classification of white blood cells. FIG. 14A is a scattergram of the detection result of a body fluid sample containing a large amount of mononuclear white blood cells. FIG. 14B is a scattergram of the detection result of a body fluid sample containing a large amount of polymorphonuclear white blood cells. FIG. 14C is a scattergram of the detection result of a body fluid sample containing mononuclear and polymorphonuclear white blood cells both in large quantities.

The white blood cell and large cell classifying step S802 during the urine analysis mode does not classify white blood cells, because urinary white blood cells are less stable in shape than white blood cells of body fluid and may be difficult to classify with high reliability. This is, however, only a non-limiting example. The urine analysis mode, as well as the body fluid analysis mode, may include the white blood cell classification.

In the fungi detecting step S803 during the urine analysis mode, fungi are detected and counted by using FSC and FLH obtained from the second measurement specimen before the sensitivity change. As compared to the white blood cell and large cell, the fungus has a smaller nucleic acid amount, and its fluorescence amount is accordingly relatively small. To detect fungi, therefore, FLH obtained in higher sensitivity than FLL is used as the fluorescence signal (FL). In order for distinction between this FLH and FLH obtained after the sensitivity change (FLH2 described later), FLH before the sensitivity change is referred to as FLH1. The fungus and white blood cell, etc. differ in their nucleic acid amounts. Hence, fungi may be efficiently counted in distinction from white blood cells, etc. by selectively using appropriate one of the fluorescence signals FLL and FLH1 that differ in detection sensitivity.

Figure 15A:
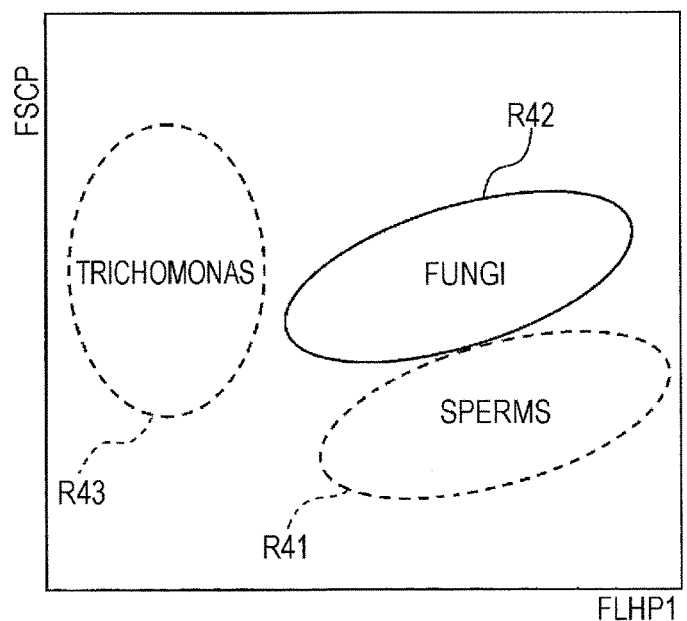
FIG. 15A is a distribution chart of fungi in the region of fluorescence light intensity-forward scattered light intensity.
Figure 15B:
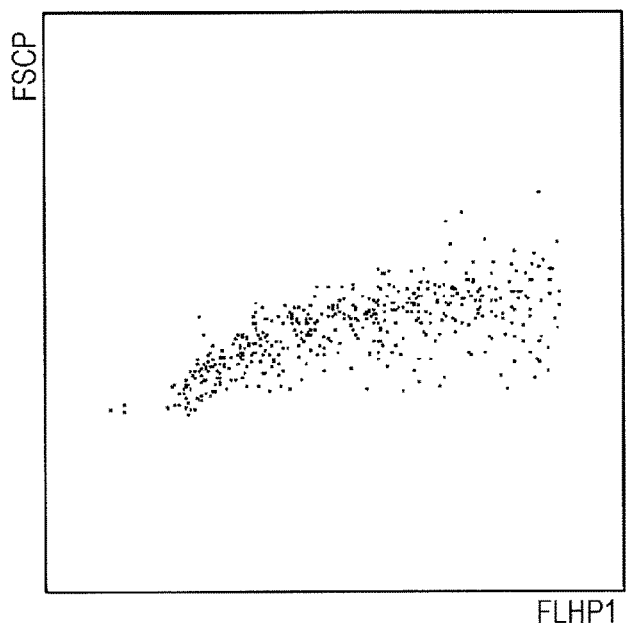
FIG. 15B is a scattergram illustrating an example of the detection result on fungi.

As illustrated in FIG. 15A, fungi are distributed in FLHP1-FSCP space. In FIG. 15A, the lateral axis represents the intensity of FLH1 (FLHP1), and the vertical axis represents the intensity of the forward scattered light signal (FSCP). The particles present in the region R42 of FIG. 15A are detected and counted as fungi. FIG. 15B illustrates an exemplified detection result on fungi.

In the anucleate element classifying step S801 during the urine analysis mode, particles present in regions R41 and R42 are detected and counted as sperms and *Trichomonas* by using FSC and FLH obtained from the fourth measurement specimen before the sensitivity change.

In the fungi detecting step S802 during the body fluid analysis mode, as with the urine analysis mode, fungi are detected and counted by using FSC and FLH obtained from the fourth measurement specimen before the sensitivity change. Neither of sperms nor *Trichomonas* is included in body fluid. These elements, therefore, are not counted in the body fluid analysis mode.

In the bacteria detecting step S804 during the urine analysis mode, bacteria are detected and counted by using FSC and FLH2 obtained from the fourth measurement specimen after the sensitivity change. The FLH2 is FLH obtained after the sensitivity change. The bacterium is even smaller than the fungus and has a smaller nucleic acid amount than the fungus, and its fluorescence amount is less than the fungus. Therefore, bacteria are detected by using FLH2 obtained in the highest sensitivity. The forward scattered light signal (FSC) used for this purpose is better in sensitivity than the forward scattered light signal (FSC) used to detect fungi and white blood cells, etc.

Figure 16:
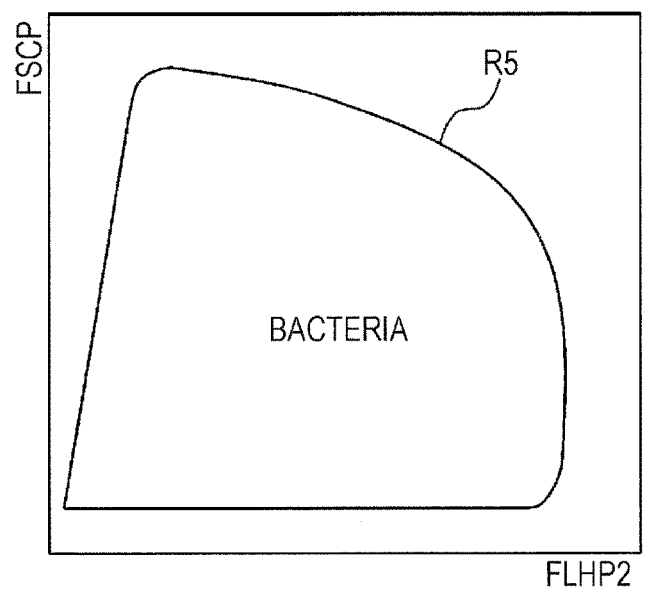
FIG. 16 is a distribution chart of bacteria in the region of fluorescence light intensity-forward scattered light intensity.

As illustrated in FIG. 16, bacteria are distributed in FLHP2-FSCP space. In FIG. 16, the lateral axis represents the intensity of the high-sensitivity fluorescence light FLH2 (FLHP2) after the sensitivity change, and the vertical axis represents the intensity of the high-sensitivity forward scattered light (FSCP). Particles present in the region R5 of FIG. 16 are detected and counted as bacteria.

In the bacteria detecting step S804 during the body fluid analysis mode, as with the urine analysis mode, bacteria are detected and counted by using FSC and FLH2 obtained from the fourth measurement specimen after the sensitivity change.

Figure 17:
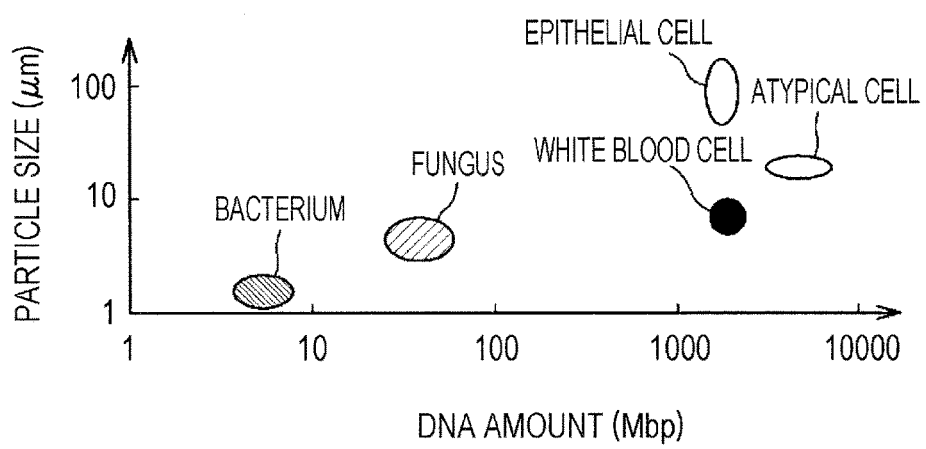
FIG. 17 is a view for explaining a relationship between a DNA amount and a particle size in each particle.

In FIG. 17 are illustrated nucleic acid amounts (DNA amounts) and particle sizes of the bacterium, fungus, white blood cell, epithelial cell, and atypical cell. As described earlier, the sample analyzer 100 may analyze, by using one measurement specimen, formed elements in urine and body fluid that largely differ in particle sizes, ranging from bacteria with very small particle sizes and less nucleic acids to epithelial cells (large cells) with large particle sizes and more nucleic acids.

To allow one optical detector 22a to accurately detect particles distributed in a broad range, the sample analyzer 100 may obtain the detection signals from the detecting unit 50 in different detection sensitivities; first detection sensitivity, second detection sensitivity, and third detection sensitivity. The first detection sensitivity is the lowest detection sensitivity, the second detection sensitivity is higher than the first detection sensitivity, and the third detection sensitivity is higher than the second detection sensitivity.

According to this embodiment, the detection signal of the first detection sensitivity is the low-sensitivity fluorescence signal (FLL) obtained before the sensitivity change. Further, the detection signal of the second detection sensitivity is the high-sensitivity fluorescence signal (FLH1) obtained before the sensitivity change, and the detection signal of the third detection sensitivity is the high-sensitivity fluorescence signal (FLH2) obtained after the sensitivity change.

The first characteristic parameter FLLA based on the low-sensitivity fluorescence signal (FLL) obtained in the first detection sensitivity is used in the white blood cell and large cell classifying step S802 as illustrated in FIG. 12A. The second characteristic parameter FLHP1 based on the high-sensitivity fluorescence signal (FLH1) obtained in the second detection sensitivity is used in the fungi detecting step S803 as illustrated in FIG. 15A. The third characteristic parameter FLHP2 based on the high-sensitivity fluorescence signal (FLH2) obtained in the third detection sensitivity is used in the bacteria detecting step S804 as illustrated in FIG. 16.

In the white blood cell and large cell classifying step S802, the fluorescence pulse area (FLLA) is used as the characteristic parameter. In the fungi detecting step S803 and the bacteria detecting step S804, the fluorescence intensities (FLHP1, FLHP2) are used as the characteristic parameter. The reason for selective uses of the fluorescence pulse area and fluorescence intensities is described below.

According to this embodiment, a beam spot formed by the light source 53 has a diameter W ranging from approximately 4 to 7 µm in a specimen flow direction. The nucleic diameters of the epithelial cell, atypical cell, and white blood cell are larger than the diameter W of the beam spot, whereas the nucleic diameters of the fungus and bacterium are smaller than the diameter W of the beam spot.

Figure 18A:
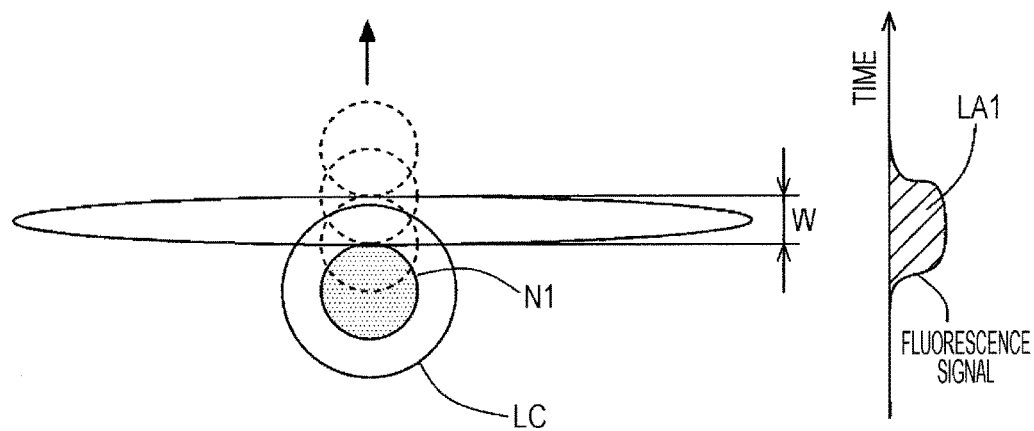
FIG. 18A is a view for explaining the pulse area of a fluorescence signal obtained from a large formed element.

As illustrated in FIG. 18A, a large cell LC has a nucleus N1 larger than the diameter W of the beam spot. Hence, the nucleus N1 fails to fall within the beam spot. The intensity of the fluorescence signal can only reflect the nucleic acid amount of a part of the light-irradiated nucleus. On the other hand, a fluorescence pulse area value LA1, which is the fluorescence signal intensity integrated by time, may be considered to be a value reflecting the nucleic acid amount of the whole nucleus. For the large cell LC, therefore, a suitable parameter reflecting the nucleic acid amount of the whole nucleus is the fluorescence pulse area value LA1 obtained by integrating the fluorescence signal intensity by time.

Figure 18B:
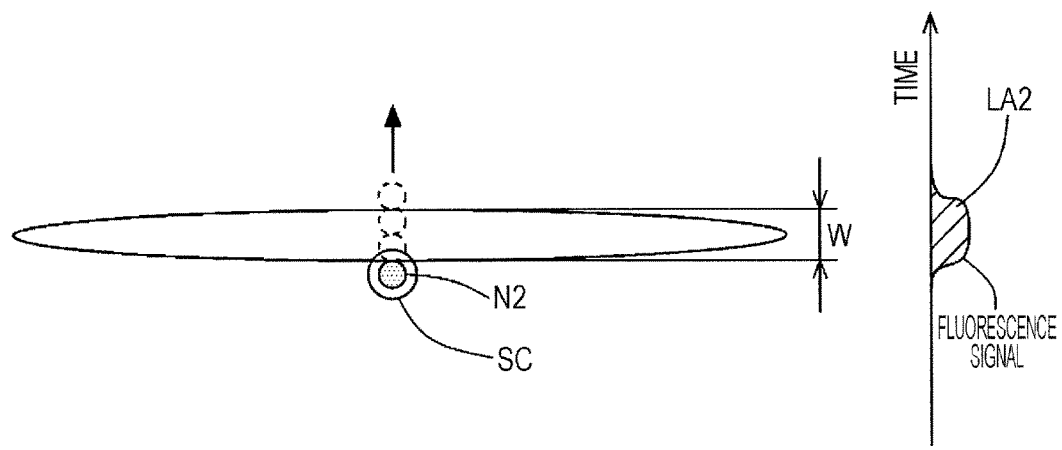
FIG. 18B is a view for explaining the pulse area of a fluorescence signal obtained from a small formed element.

As illustrated in FIG. 18B, a small cell SC, such as a fungus, has a nucleus N2 smaller than the diameter W of the beam spot. Hence, the whole nucleus N2 of the cell SC falls within the beam spot. The whole particle of a small cell, such as fungus or bacterium, falls within the beam spot. When the cell SC moves in its moving direction, light is emitted on the whole nucleus N2 during the time when the nucleus N2 enters the beam spot and moves out of there. Therefore, if the area value LA2 obtained by integration of the fluorescence signal intensity by time, is used as the parameter reflecting the nucleic acid amount of the small cell SC, its apparent value results in a larger value than the actual nucleic acid amount. On the other hand, the fluorescence signal intensity may be considered to be a value reflecting the actual nucleic acid amount of the nucleus. For the small cell SC, therefore, a suitable parameter reflecting the actual nucleic acid amount is the fluorescence light intensity.

The white blood cell is approximately 10 to 15 m in diameter, and the fungus (non-sprouted) is approximately 3 to 8 µm in diameter. The white blood cell and fungus having similar sizes may be not very easy to distinguish from each other. According to this embodiment, however, white blood cells and fungi may be counted in distinction from each other. This embodiment selectively uses appropriate one of the fluorescence signals FLL and FLH1 that differ in detection sensitivity for the white blood cells and fungi. This embodiment further uses the fluorescence light pulse area for white blood cells, while using the fluorescence light intensity for small cells, fungi, to facilitate distinction between white blood cells and fungi based on their different nucleic acid amounts.

The classification and counting result analyzing and displaying step S510 during the urine analysis mode is described referring to FIG. 6 again. In this step, the CPU 401 displays on the display unit 409 classification and counting result screens including classification and counting results and scattergram of urinary formed elements. The counting result displayed on the counting result screen include the counts of red blood cells, white blood cells, casts, epithelial cells, bacteria, fungi, sperms, *Trichomonas*, and atypical cells.

In the classification and counting result analyzing and displaying step S510 during the body fluid analysis mode, the CPU 401 carries out the processing steps illustrated in FIG. 19. These steps may determine any inflammations suspected from the analysis results (counting results) of different types of particles included in the body fluid, specifically, based on a combination of particles exhibiting abnormal values among the different types of particles.

In step S851, the CPU 401 determines the type of a received body fluid. When the body fluid is cerebrospinal fluid, the CPU 401 determines in S852 on any inflammations in accordance with criteria defined for cerebrospinal fluid. When the body fluid is synovial fluid, the CPU 401 determines in S853 on any inflammations in accordance with criteria defined for synovial fluid. When the body fluid is coelomic fluid, the CPU 401 determines in S854 on any inflammations in accordance with one or more criteria defined for coelomic fluid. For the non-specified body fluid, the CPU 401 determines in S855 whether any of the criteria used in S852 to S854 is applicable to the body fluid. The criteria used in S852 to S854 are preset in the hard disc 404.

The plural criteria used to determine on inflammations associated with cerebrospinal fluid in S 852 are the following criteria A1 to A4. These criteria are illustrated herein as a non-limiting example, and threshold values included in the criteria may be suitably decided by users.

First criterion A1 for determining bacterial meningitis suspected: "1,000 or more white blood cells per µL", "predominant polymorphonuclear leukocytes", and "1,000 or more bacteria per µL".

Second criterion A2 for determining fungal meningitis suspected: "100 or more white blood cells per µL", "predominant mononuclear leukocytes", and "100 or more fungi per µL".

Third criterion A3 for determining viral meningitis suspected: "10 or more white blood cells per µL", "predominant mononuclear leukocytes", and "neither of the first criterion A1 nor the second criterion A2 is fulfilled".

Fourth criterion A4 for determining neoplastic meningitis suspected: "10 or more atypical cells per µL".

The term, "predominant", refers to either one of mononuclear leukocytes and polymorphonuclear leukocytes that account for a larger proportion than the other in the total count of white blood cells. Comparing the percentage of mononuclear leukocytes (MN %) and the percentage of polymorphonuclear leukocytes (PMN %), mononuclear leukocytes are predominant with MN %>PMN %, while polymorphonuclear leukocytes are predominant with MN %≤PMN %. In normal spinal fluid, the vast majority (approximately 98%) of white blood cells are mononuclear leukocytes, however, polymorphonuclear leukocytes become predominant in cases with bacterial meningitis.

In S853, plural criteria for determining inflammations associated with synovial fluid are, for example, the following criteria B1 and B2.

Second criterion B1 for determining suppurative arthritis suspected: "1,000 or more white blood cells per µL", "1,000 or more bacteria per µL", and "1,000 or more fungi per µL".

First criterion B2 for determining crystal induced arthritis suspected: "100 or more white blood cells per µL", and "10,000 or more crystals per µL".

In S854, plural criteria for determining inflammations associated with coelomic fluid in step S854 are, for example, the following criteria C to C3.

First criterion C1 for determining bacterial inflammation suspected: "1,000 or more white blood cells per µL", "predominant polymorphonuclear leukocytes", and "1,000 or more bacteria per µL".

Second criterion C2 for determining fungal inflammation suspected: "100 or more white blood cells per µL", "predominant mononuclear leukocytes", and "100 or more fungus per µL".

Third criterion C3 for determining neoplastic inflammation suspected: "10 or more atypical cells per µL".

In step S856, the CPU 401 determines whether any inflammation should be suspected. Confirming that the inflammation should be suspected, the CPU 401, in S857, appends a suspect message to the determination result. In the event that the body fluid sample is "non-specified" and fulfills any of the criteria, information on the fulfilled criterion (criteria) is appended to the result in place of the suspect message.

In S858, the CPU 401 determines whether hemorrhage should be suspected based on the following criterion D1.

Criterion D1 for determining hemorrhage suspected: "1,000 or more red blood cells per PL".

Confirming that the hemorrhage should be suspected, the CPU 401, in S859, appends a red blood cell correction message to the determination result to suggest that red blood cells should be corrected.

In S860, the CPU 401 displays, on the display unit 409, a counting result screen including the counting result and a determination result screen including the determination result. As with the urine analysis mode, the counting result screen includes the counting result and scattergram. The counting result displayed on the counting result screen in the body fluid analysis mode includes the counts of red blood cells, white blood cells, mononuclear leukocytes (MN), polymorphonuclear leukocytes (PMN), nucleated cells (TNC), large cells (LC), bacteria, fungi, and atypical cells. The screen further includes the percentage of mononuclear leukocytes (MN %) and the percentage of polymorphonuclear leukocytes (PMN %).

Figure 20:
FIG. 20 shows a determination result display screen including a suspect message.

In S857, the CPU 401, in response to the determination result with the suspect message appended thereto, further displays a determination result screen including the suspect message. FIG. 20 illustrates an exemplified determination result display screen.

As illustrated in FIG. 20, the determination result screen includes the sample ID, type of a target body fluid, suspect message obtained as the determination results of S852 to S854, and classification and counting results supporting the determination result. The suspect message of the illustrated example is "bacterial meningitis ?" indicating that bacterial meningitis is suspected. In this example are further displayed the count of white blood cells, percentage of white blood cells, and count of bacteria supporting the determination result. These pieces of information assist a user who operates the analyzer when determining whether the inflammation should be suspected based on the classification and counting results.

Figure 21:
FIG. 21 shows a determination result display screen including a red blood cell correction message.

In S859, the CPU 401, in response to the determination result with the red blood cell correction message appended thereto, further displays a determination result screen including the red blood cell correction message. FIG. 21 illustrates an exemplified determination result display screen.

As illustrated in FIG. 21, the determination result screen includes the sample ID, type of a target body fluid, red blood cell count, white blood cell count, and correction-suggesting message. The determination result screen further includes a YES button to approve the correction, and a NO button to reject the correction.

The spinal fluid and synovial fluid collected by puncturing a needle into a body may entrap through the punctured needle blood (peripheral blood) containing white blood cells. In such a case, accurate counting of white blood cells in the body fluid may fail unless white blood cells included in the entrapped blood are subtracted. To this end, the count of white blood cells may be corrected based on the count of red blood cells, if they are included in a large amount beyond a threshold value, to obtain an accurate count of white blood cells.

When YES illustrated in FIG. 21 is selected in S861, the CPU 401, in S862, corrects the count of white blood cells based on the count of red blood cells in accordance with the formula below.

$$WBC^* = WBC - (RBC/F)$$

In the formula, WBC* is the corrected count of white blood cells, and F is a value optionally set by a user, indicating the count of red blood cells per one white blood cell included in peripheral blood. Suitably F=480 to 1,100.

When the count of red blood cells ($RBC_{B1}$) and the count of white blood cells ($WBC_{B1}$) in a subject's peripheral blood are known, these count values may be inputted to correct red blood cells in accordance with the formula below.

$$WBC^* = WBC - (WBC_{B1}/RBC_{B1}) \times RBC$$

In S863, the CPU 401 additionally displays, on the counting result screen, the count of white blood cells resulting from the correction of red blood cells. Then, the CPU 401 ends the operation.

After the determination result is displayed, the CPU 401 may still receive from a user an instruction to change the selected body fluid sample. For example, if the user incorrectly selects coelomic fluid as the body fluid sample to be measured and notices his/her error on the displayed determination result, the user may correct the selected body fluid sample. This can only be accepted before the counting result is validated. When the body fluid sample is corrected by the user, step S851 is carried out again to determine on inflammations suspected in the newly selected body fluid.

None of the conventional sample analyzers available so far is equipped to count white blood cells and fungi in body fluid. According to this embodiment, one sample analyzer 100 may count white blood cells and fungi both in body fluid. In the case of abnormally high values exhibited for white blood cells and fungi in spinal fluid, a user may suspect fungal meningitis (cryptococcal meningitis).

The sample analyzer 100 according to this embodiment counts white blood cells and fungi by using the measurement specimen containing hemolyzed red blood cells of body fluid. The fungi and red blood cells are alike in size, and the body fluid may contain more red blood cells than urine. According to this embodiment wherein red blood cells are hemolyzed, fungi may be very accurately counted without being affected by red blood cells.

The sample analyzer 100 according to this embodiment, by this device alone, may count white blood cells, fungi, and bacteria in body fluid. In the case of an abnormally high value exhibited for white blood cells when, for example, spinal fluid is analyzed, the counts of bacteria and fungi may be further checked to assist a user in diagnosing whether a subject has bacterial meningitis or fungal meningitis.

The sample analyzer 100 according to this embodiment may classify white blood cells in body fluid into mononuclear leukocytes and polymorphonuclear leukocytes. It is clinically important in body fluid tests, as well as the count of white blood cells, to determine which of mononuclear leukocytes and polymorphonuclear leukocytes is predominant. According to this embodiment, useful information for body fluid tests may be provided by such classification of white blood cells.

The sample analyzer 100 according to this embodiment may classify white blood cells and further count bacteria and fungi. Typical *meningitides* that may be identified by spinal fluid tests are bacterial meningitis, fungal meningitis, and viral meningitis. Of these examples, bacterial meningitis may be distinguished from the other *meningitides* based on criteria; significantly increased white blood cells and decreased mononuclear cells. On the other hand, fungal meningitis and viral meningitis both exhibiting increased white blood cells may be difficult to discern by their percentages of white blood cells alone. According to this embodiment, however, fungi, as well as white blood cells, may be counted, and the count of fungi may be taken into account when determining whether or not the inflammation is fungal meningitis. With fewer fungi, viral meningitis may be suspected. Further advantageously, viral meningitis may be more accurately diagnosed by using the count of bacteria in addition to the count and percentage of white blood cells. According to this embodiment, therefore, pieces of information useful for diagnoses of *meningitides* may be presented at once with one sample analyzer.

[Another Example of Red Blood Cell and Crystal Counting Method]

Another method for counting red blood cells and crystals in body fluid is hereinafter described referring to FIG. 22. According to the embodiment described so far, FLH and FSC are used for distinction between red blood cells and crystals as illustrated in FIG. 19. Instead, depolarized side scattered light PSS may be used for distinction between red blood cells and crystals.

Figure 22A:
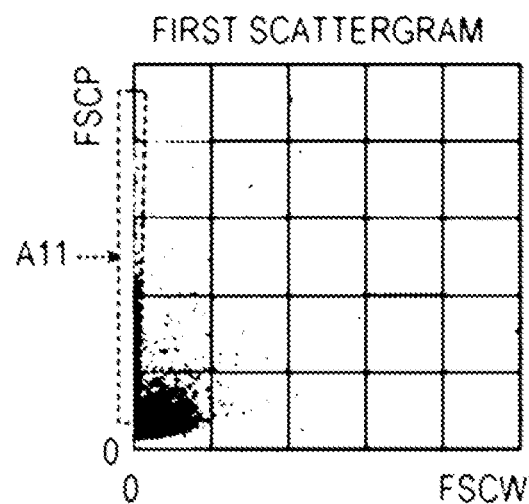
FIGS. 22A and 22B are scattergrams for use in counting red blood cells and crystals.

As illustrated in FIG. 22A, the CPU 401 of the processing unit 13 plots particles on a first scattergram with its two axes respectively representing the pulse width of the forward scattered light signal (FSCW) and the intensity of the forward scattered light signal (FSCP) based on the characteristic parameters obtained in the anucleate element measuring step S505. Then, a fixed region A11 is defined on the first scattergram.

Referring to FIG. 22A, the region A11 is a region with red blood cells and crystals included in the first or third measurement specimen, and any region but the region A1 is a region with dust and bacteria, etc. included in the measurement specimen. The CPU 401 extracts particles present in the region A11 on the first scattergram.

Figure 22B:
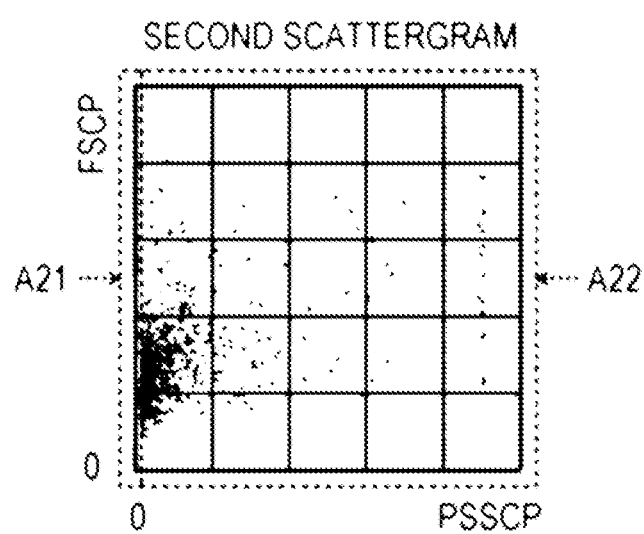

As illustrated in FIG. 22B, the CPU 401 plots the particles extracted from the region A11 on a second scattergram with its two axes respectively representing the intensity of the depolarized side scattered light signal (PSSCP) and the intensity of the forward scattered light signal (FSCP). Then, fixed regions A21 and A22 are defined on the second scattergram.

Referring to FIG. 22B, PSSCP on the lateral axis indicates, of the side scattered light emitted from the particles, an amount of polarized light perpendicular to irradiated light that is a depolarization degree. As compared to red blood cells, crystals are more likely to depolarize light and accordingly distributed in a region with large PSSCP values. The regions A21 and A22 illustrated in FIG. 22B are respectively regions with red blood cells and crystals. The CPU 401 counts the particles present in the region A21 as red blood cells, while counting the particles present in the region A22 as crystals.

A red blood cell and crystal are both anucleate elements and alike in size. In any sample containing a large amount of crystals, therefore, the crystals possibly adversely affect the accuracy of classifying red blood cells. The depolarized side scattered light may allow for accurate distinction between red blood cells and crystals because red blood cells hardly depolarize light, whereas anisotropic crystals are apt to depolarize light. This may lead to higher accuracy in counting red blood cells even in urine samples heavily containing crystals. Further, synovial fluid may contain crystals and entrap blood when collected from a body. Therefore, more accurate distinction between red blood cells and crystals is helpful in making accurate diagnoses associated with synovial fluid.

Other Embodiment

The particle counting function in the body fluid analysis mode, inflammation determining function based on the elements in body fluid, and white blood cell correcting function based on red blood cell count according to the embodiment described so far are applicable to body fluid analyses using a blood cell counter.

The measuring unit 12 and the processing unit 13 may be integrally formed. For example, the processing unit 13 may be incorporated in the measuring unit 12.

What is claimed is:

1. A sample analyzer for analyzing a sample, comprising:
a preparing unit including a suction tube that suctions a sample and a reaction tank that receives the sample suctioned by the suction tube, wherein the sample is mixed with a surfactant-containing diluent, and a nucleic acid staining reagent in the reaction tank to prepare a measurement specimen in which nucleic acids of nucleated cells are stained and red blood cells are hemolyzed;
a detecting unit including a light source that irradiates particles included in the measurement specimen with light and an optical detector that receives scattered light emitted from the particles to output scattered light signal and receives fluorescence light emitted from the particles to output a fluorescence signal; and
a processer programmed to perform operations, comprising:
deriving, from the scattered signal, a scattered light parameter reflecting particle size and deriving, from the fluorescence signal, a first characteristic parameter reflecting a nucleic acid amount and a second characteristic parameter reflecting another nucleic acid amount, the second characteristic parameter being different from the first characteristic parameter, wherein
the scattered light parameter includes a scattered light pulse width and a scattered light intensity;
counting white blood cells based on the first characteristic parameter and the pulse width of the scattered light parameter; and
counting fungi based on the second characteristic parameter and the the scattered light peak of the scattered light parameter.

2. The sample analyzer according to claim 1, wherein the processor is programmed to count] nucleated cells larger than the white blood cells in the sample based on the detection signal.

3. The sample analyzer according to claim 1, wherein the processor is programmed to distinguish the white blood cells and the nucleated cells larger than the white blood cells in the sample at least from the fungi and bacteria in the sample based on the detection signal to obtain a total count of the white blood cells and the nucleated cells larger than the white blood cells.

4. The sample analyzer according to claim 1, wherein the detection signal includes a fluorescence signal obtained from the fluorescence light emitted from the particles, and the processor is programmed to count the white blood cells using a first characteristic parameter being obtained from the fluorescence light and reflecting nucleic acid amount, and count the fungi using a second characteristic parameter different from the first characteristic parameter, the second characteristic parameter being obtained from the fluorescence signal and reflecting the nucleic acid amount.

5. The sample analyzer according to claim 4, wherein the first characteristic parameter is a fluorescence light pulse area obtained from the fluorescence signal, and the second characteristic parameter is a fluorescence light intensity obtained from the fluorescence signal.

6. The sample analyzer according to claim 4, wherein the detecting unit is operable to output the fluorescence signal in a first detection sensitivity and a second detection sensitivity higher than the first detection sensitivity, and
the processor is programmed to obtain the first characteristic parameter from the fluorescence signal outputted in the first detection sensitivity, and obtain the second characteristic parameter from the fluorescence signal outputted in the second detection sensitivity.

7. The sample analyzer according to claim 1, wherein the processor is programmed to classify the white blood cells into mononuclear leukocytes and polymorphonuclear leukocytes based on the detection signal.

8. The sample analyzer according to claim 1, wherein the processor is programmed to count the bacteria in the sample based on the detection signal.

9. The sample analyzer according to claim 8, wherein the detecting unit is operable to output the detection signal by detecting the fluorescence light in the first detection sensitivity, the second detection sensitivity higher than the first detection sensitivity, and a third detection sensitivity higher than the second detection sensitivity, and
the processor is programmed to count the white blood cells using a characteristic parameter of the detection signal outputted in the first detection sensitivity, count the fungi using a characteristic parameter of the detection signal outputted in the second detection sensitivity, count the bacteria using a characteristic parameter of the detection signal outputted in the third detection sensitivity.

10. The sample analyzer according to claim 1, wherein the preparing unit prepares, from a portion of the sample, the measurement specimen in which the red blood cells are hemolyzed, and mixes a remaining portion of the sample with a reagent to prepare a non-hemolyzed measurement specimen in which red blood cells are not hemolyzed,
the detecting unit irradiates particles included in the non-hemolyzed measurement specimen with light to receive scattered light and fluorescence light emitted from the particles and output a detection signal, and
the processor is programmed to count red blood cells in the sample based on the detection signal obtained from the non-hemolyzed measurement specimen.

11. The sample analyzer according to claim 10, wherein the processor is programmed to count crystals in the sample based on the detection signal obtained from the non-hemolyzed measurement specimen.

12. The sample analyzer according to claim 1, wherein the sample analyzer is operable in a urine analysis mode for analyzing a urine sample and in a body fluid analysis mode for analyzing a body fluid sample other than blood and urine, and
the processor is programmed to classify and counts particles in a measurement specimen in the body fluid analysis mode for a counting target item different from a counting target item in the urine analysis mode.

13. The sample analyzer according to claim 1, wherein the sample is a body fluid sample other than blood and urine, and
the processor is programmed to determine a meningitis, an arthritis, or an inflammation of coelomic membrane based on a counting result of the particles included in the body fluid sample.

14. The sample analyzer according to claim 1, wherein the processor is programmed to receive an designation of a type of the sample from a plurality of types and determine the inflammation based on a criterion according to the designated type of the sample.

15. A sample analyzing method, comprising:
mixing a sample, a surfactant-containing diluent, and a nucleic acid staining reagent to prepare a measurement specimen in which nucleic acids of nucleic cells are stained and red blood cells are hemolyzed;
irradiating particles included in the measurement specimen to receive scattered light signal and fluorescence light signal emitted from the particles and output a detection signal; and
counting white blood cells and fungi in the sample based on the detection signal, wherein the counting comprising executing a programmed stored in a memory by a processor to analyze the detected signal by carrying out the following operations:
deriving, from the scattered light signal, a scattered light parameter reflecting particle size and deriving, from the fluorescence light signal, a first characteristic parameter reflecting a nucleic acid amount and a second characteristic parameter reflecting another nucleic acid amount, the second characteristic parameter being different from the first characteristic parameter, wherein the scattered light parameter includes a scattered light pulse width and a scattered light intensity;
counting the white blood cells based on the first characteristic parameter and the pulse width of the scattered light parameter; and
counting the fungi based on the second characteristic parameter and the the scattered light peak of the scattered light parameter.

16. A sample analyzer for analyzing a sample, the analyzer comprising:
a preparing unit including a suction tube that suctions a sample and a reaction tank that receives a sample suctioned by the suction tube, wherein the sample is mixed with a surfactant-containing diluent, and a nucleic acid staining reagent in the reaction tank to prepare a measurement specimen in which nucleic acids of nucleated cells are stained and red blood cells are hemolyzed;
a detecting unit including a light source that irradiates particles included in the measurement specimen with light and an optical detector that to receive scattered light emitted from the particles to output scattered light signal and receives fluorescence light emitted from the particles to output a fluorescence signal; and a processing unit that comprises a processor which executes a program stored in a memory to obtain plural characteristic parameters from the detection signal outputted from the detecting unit, distinguishes white blood cells in the sample at least from large nucleated cells and fungi based on a first combination of plural characteristic parameters reflecting particle sizes and nucleic acid amounts, and classifies the white blood cells in the sample at least into mononuclear leukocytes and polymorphonuclear leukocytes based on a second combination of plural characteristic parameters different from the first combination, wherein the distinguishing of the white blood cells and the fungi includes performing the following operations by the processor:

deriving, from the scattered light signal, a scattered light parameter reflecting particle size and deriving, from the fluorescence light signal, a first characteristic parameter reflecting a nucleic acid amount and a second characteristic parameter reflecting another nucleic acid amount, the second characteristic parameter being different from the first characteristic parameter, wherein the scattered light parameter includes a scattered light pulse width and a scattered light intensity;

counting the white blood cells based on the first characteristic parameter and the pulse width of the scattered light parameter; and counting the fungi based on the second characteristic parameter and the the scattered light peak of the scattered light parameter.

\* \* \* \* \*